United States Patent
Cendrillon et al.

(10) Patent No.: US 9,814,400 B1
(45) Date of Patent: Nov. 14, 2017

(54) METHOD FOR IMPROVING ACCURACY OF PULSE RATE ESTIMATION

(71) Applicant: Verily Life Sciences LLC, Mountain View, CA (US)

(72) Inventors: Raphael Cendrillon, Mountain View, CA (US); Christopher Towles Lengerich, Palo Alto, CA (US); Mark Murphy, Palo Alto, CA (US); Ali Shoeb, Mill Valley, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 230 days.

(21) Appl. No.: 14/721,078

(22) Filed: May 26, 2015

(51) Int. Cl.
*A61B 5/00* (2006.01)
*A61B 5/024* (2006.01)
*G06F 19/00* (2011.01)
*A61B 5/022* (2006.01)
*A61B 5/0245* (2006.01)
*A61B 5/0295* (2006.01)

(52) U.S. Cl.
CPC .......... *A61B 5/02438* (2013.01); *A61B 5/022* (2013.01); *A61B 5/0245* (2013.01); *A61B 5/0295* (2013.01); *A61B 5/02416* (2013.01); *A61B 5/721* (2013.01); *A61B 5/7221* (2013.01); *A61B 5/7278* (2013.01); *G06F 19/3406* (2013.01)

(58) Field of Classification Search
CPC . A61B 5/02438; A61B 5/02416; A61B 5/721; A61B 5/7278; A61B 5/0245; A61B 5/0295; A61B 5/7221; A61B 5/022; G06F 19/3406
See application file for complete search history.

(56) References Cited

U.S. PATENT DOCUMENTS

| | | | |
|---|---|---|---|
| 4,063,551 | A | 12/1977 | Sweeney |
| 5,485,395 | A | 1/1996 | Smith |
| 5,776,070 | A | 7/1998 | Kitazawa et al. |
| 5,797,840 | A | 8/1998 | Akselrod et al. |
| 6,122,535 | A | 9/2000 | Kaestle et al. |
| 6,289,238 | B1 | 9/2001 | Besson et al. |
| 6,574,491 | B2 | 6/2003 | Elghazzawi |

(Continued)

FOREIGN PATENT DOCUMENTS

WO 2012/073069 6/2012

*Primary Examiner* — Rex R Holmes
(74) *Attorney, Agent, or Firm* — McDonnell, Boehnen, Hulbert, & Berghoff LLP

(57) ABSTRACT

Systems and methods are provided for determining the frequency of a cardiovascular pulse based on a photoplethysmographic measurement of blood in a portion of subsurface vasculature. A plurality of samples of the photoplethysmographic signal are obtained and a frequency spectrum determined based on a first set of the plurality of samples. A frequency is determined based on a maximum frequency component of the frequency spectrum. Further, a confidence level of the determined frequency of the maximum frequency component is determined based on the magnitude of the maximum frequency component and the overall energy in the frequency spectrum. A pulse rate is then determined by updating a predicted pulse rate of a second, earlier set of the plurality of samples based on the frequency of the maximum frequency component and the determined confidence level.

20 Claims, 11 Drawing Sheets

(56) References Cited

U.S. PATENT DOCUMENTS

| | | |
|---|---|---|
| 7,072,702 B2 | 7/2006 | Edgar, Jr. et al. |
| 7,740,588 B1 | 6/2010 | Sciarra |
| 8,298,154 B2 | 10/2012 | Hete et al. |
| 8,527,038 B2 | 9/2013 | Moon et al. |
| 2009/0105556 A1 | 4/2009 | Fricke et al. |
| 2009/0216499 A1 | 8/2009 | Tobola et al. |
| 2013/0006123 A1 | 1/2013 | Aoshima |
| 2014/0364750 A1 | 12/2014 | Brumfield et al. |
| 2015/0019170 A1 | 1/2015 | Solem et al. |
| 2015/0173627 A1* | 6/2015 | Fujii .................. A61B 5/02416 600/483 |

* cited by examiner

METHOD FOR IMPROVING ACCURACY OF PULSE RATE ESTIMATION

BACKGROUND

Unless otherwise indicated herein, the materials described in this section are not prior art to the claims in this application and are not admitted to be prior art by inclusion in this section.

A variety of cardiovascular parameters can be detected by illuminating blood in a portion of subsurface vasculature and detecting one or more properties of light responsively emitted from the portion of subsurface vasculature (e.g., reflected, fluorescently re-emitted, scattered, or otherwise emitted from). Such cardiovascular parameters can include a volume of blood over time, a pulse rate of blood, a flow rate of blood over time, a blood pressure, an oxygen saturation, or some other properties of blood in the portion of subsurface vasculature at one or more points in time. Such cardiovascular parameters can be detected over a protracted period of time, e.g., using a body-mountable device, to determine a health state of a person.

SUMMARY

Some embodiments of the present disclosure provide a method including: (i) receiving a plurality of samples of a signal that is related to a cardiovascular pulse; (ii) determining a predicted pulse rate based at least on a first set of the plurality of samples; (iii) determining a frequency spectrum of a second set of the plurality of samples, wherein the frequency spectrum includes a plurality of frequency components, each having a respective magnitude; (iv) determining a frequency of a local maximum of the frequency spectrum; (v) determining an overall energy in the frequency spectrum; (vi) determining a confidence level of the determined frequency of the local maximum based on at least a magnitude of the local maximum of the frequency spectrum and the determined overall energy in the frequency spectrum; and (vii) determining a pulse rate based on the predicted pulse rate, the determined frequency of the local maximum, and the determined confidence level.

Some embodiments of the present disclosure provide a system including: (i) a sensor configured to detect a signal that is related to a cardiovascular pulse; and (ii) a controller that is operably coupled to the sensor and that includes a computing device programmed to perform controller operations including: (a) operating the sensor to obtain a plurality of samples of the signal; (b) determining a predicted pulse rate based at least on a first set of the plurality of samples; (c) determining a frequency spectrum of a second set of the plurality of samples, wherein the frequency spectrum includes a plurality of frequency components, each having a respective magnitude; (d) determining a frequency of a local maximum of the frequency spectrum; (e) determining an overall energy in the frequency spectrum; (f) determining a confidence level of the determined frequency of the local maximum, wherein the determined confidence level is based on at least a magnitude of the local maximum of the frequency spectrum and the determined overall energy in the frequency spectrum; and (g) determining a pulse rate based on the predicted pulse rate, the determined frequency of the local maximum, and the determined confidence level.

These as well as other aspects, advantages, and alternatives, will become apparent to those of ordinary skill in the art by reading the following detailed description, with reference where appropriate to the accompanying drawings.

DETAILED DESCRIPTION

Figure 1A:
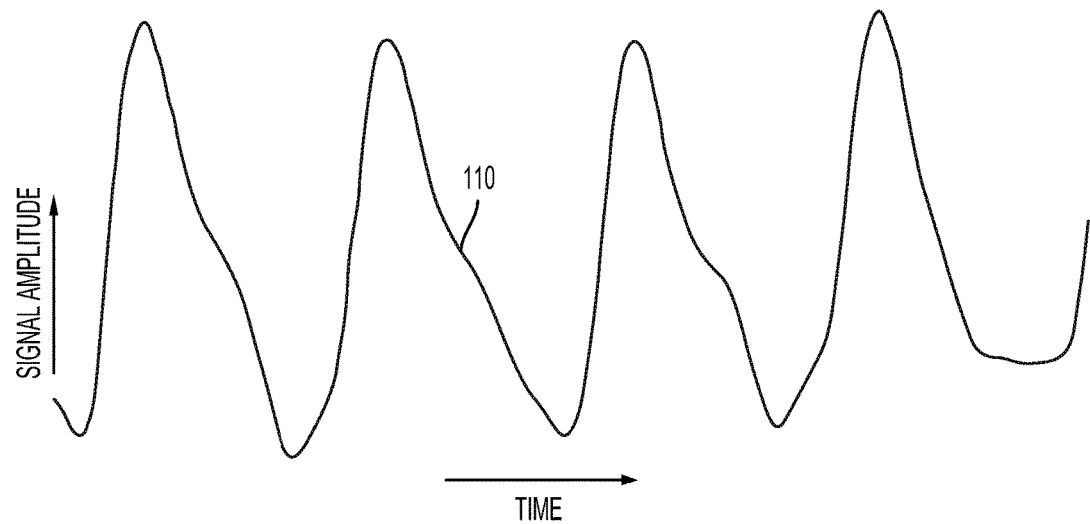
FIG. 1A is an example of a detected signal containing an oscillating pattern.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where detection of the frequency and/or rate of oscillating patterns in biosignals (e.g., determining a breathing rate, determining a gait cycle frequency) or other signals of interest is desired. The signals of interest could be detected from any living or non-living body or a portion thereof or from some other environment and/or variable or parameter of interest.

I. OVERVIEW

In some applications the frequency of an oscillating pattern in a detected signal can be related to a property of interest. For example, a volume of blood in a portion of subsurface vasculature could include an oscillating pattern (e.g., a pattern of absorption of light by blood in a portion of subsurface vasculature related to the volume of blood in the portion of subsurface vasculature) related to a cardiovascular pulse (e.g., a rate of pulses of blood in the portion of subsurface vasculature, a rate of occurrence of electrical events related to activity of a heart). Such a volume of blood could be detected photoplethysmographically, by illuminating the portion of subsurface vasculature and detecting a degree of absorption of the illumination over time, e.g., by a light emitter and light detector of a body-mountable device (e.g., a wearable wrist-mountable device). The pulse rate of the cardiovascular pulse could be determined by determining a frequency of the oscillating pattern. Other properties could be related to the frequency of oscillating patterns in other detected signals The frequency of such oscillating patterns could be determined in a variety of ways. In some examples, a frequency spectrum of a plurality of samples of a signal could be determined (e.g., using a discrete Fourier transform). The frequency of oscillating patterns in the signal could be determined based on a frequency of a peak or other feature within such a determined frequency spectrum. For example, the frequency of an oscillating pattern could be determined by identifying the frequency component of a frequency spectrum that has the greatest magnitude of all of the frequency components of the frequency spectrum. The frequency resolution of a frequency (e.g., a pulse rate) determined through such a method could be increased through a variety of methods, e.g., by zero-padding the plurality of samples of the signal before calculating the frequency spectrum, by fitting a sinc function to frequency components of the frequency spectrum that are proximate the frequency of a peak of the frequency spectrum, or by some other method.

Such methods for determining the frequency of contents of a signal of interest (e.g., of determining a pulse rate of a signal related to a cardiovascular pulse) could be performed on a signal of interest at a plurality of points in time, e.g., to provide respective estimates of the frequency of the signal contents at the plurality of points in time. Further, determined frequencies could be improved (e.g., could have an increased accuracy, a decreased noise) based on previously determined frequencies and/or frequencies determined based on samples of the detected signal that are detected earlier in time. For example, a frequency of contents of a first set of samples of a signal could be determined based on a first frequency spectrum based on the first set of samples and on a frequency estimate determined based on a second, earlier set of samples of the signal. Such a determination could include determining a weighted combination of a first frequency (determined from a frequency spectrum of a first set of samples) and a second frequency (determined from a second set of samples corresponding to points in time prior to points in time corresponding to the first set of samples). This could include using the first frequency to update the second frequency, e.g., using an alpha-beta filter.

In some examples, such first and second frequencies could be combined according to a weighting that is related to a measure of the quality of the determined first and/or second frequency (e.g., a measure of the expected noise and/or inaccuracy of the first and/or second frequency). For example, a weighting factor could be determined based on a magnitude of a peak or other feature of a determined frequency spectrum from which the first frequency is determined (e.g., a magnitude or squared magnitude of a maximum frequency component of a frequency spectrum) divided by or otherwise normalized by a measure of the overall energy in the frequency spectrum (e.g., a sum of the squared magnitude of all of the frequency components of the frequency spectrum). Such a weighting factor could be determined and/or applied to first and second determined frequencies such that, when the confidence or other determined quality of the first frequency is greater, the weighted combination of the first and second frequencies is more weighted toward the first frequency. Other methods of determining a weighted combination of two or more determined frequencies, based on a determined measure of the confidence and/or quality of one or more such determined frequencies, are anticipated.

In some examples, such multiple estimates of the frequency of contents of a detected signal, based on respective different sets of samples of the detected signal, could be determined based on overlapping sets of samples of the detected signal. This could include partitioning samples of the signal of interest into overlapping windows (e.g., approximately ten-second-long windows overlapping by approximately 1 second) and determining respective frequency spectra and/or respective determined frequencies (e.g., pulse rates) based on such spectra for each of the overlapping windows. In some examples, such overlapping windows could differ by a single sample, i.e., could be shifted in time by a single sample. In such examples, a frequency of contents of the detected signal could be detected for each sample, e.g., as each sample of the signal is detected over time. In such examples, a frequency spectrum for a first set of samples of the detected signal could be determined by updating a frequency spectrum determined for a second set of samples that are shifted in time relative to the first set of samples (e.g., by a single sample) using a sliding discrete Fourier transform algorithm. Further, in applications wherein the frequency of an oscillating pattern of interest is likely to have a value within a specified range (e.g., a pulse rate likely to be within approximately 0.5 Hertz and approximately 3.5 Hertz, i.e., approximately 30 beats per minute and approximately 200 beats per minute), only those frequency components of the frequency spectrum that are within the specified range could be determined.

In some examples, a motion artifact or other noise signal present in the signal of interest could be removed before and/or after determining a frequency spectrum from samples of the detected signal to determine a frequency (e.g., pulse rate) of the signal of interest. This could include using information about the noise signal detected using a sensor or other means. For example, a noise signal in a photoplethysmographic (PPG) blood volume signal could be related to motion of a portion of subsurface vasculature relative to a sensor (e.g., relative to a light emitter and/or light detector of a PPG sensor). An accelerometer (e.g., an accelerometer of a body-mountable device that also includes the light emitter and/or light detector of the PPG sensor) could be used to generate an artifact signal related to the motion artifact in the PPG blood volume signal. The generated artifact signal could be used to filter the PPG signal, e.g., by using a least mean squares (LMS) filter. Additionally or alternatively, a frequency spectrum of the artifact signal could be generated and used to filter a determined frequency spectrum of the detected signal (e.g., using an LMS filter for each of the frequency components of the frequency spectra).

Other artifact signals could be detected by other means and used to filter a signal of interest in other ways.

The methods described herein to determine a frequency (e.g., a pulse rate) of a signal of interest could be applied to a variety of signals detected by a variety of means. In some examples, the signal of interest could be a blood volume signal, a blood flow rate signal, a blood oxygen saturation signal, a heart electrical activity signal, a blood pressure signal, or some other signal related to a cardiovascular pulse, and the determined frequency could be a pulse rate of the cardiovascular pulse. Such signals could be detected using a PPG sensor, an electrocardiographic (ECG) sensor (e.g., two or more electrodes), a tonometer, a blood pressure cuff, or some other sensor(s). In some examples, the signal of interest could be some other signal, e.g., a signal relating to respiration (e.g., a detected strain of a strap mounted around a person's chest), a signal relating to a repeated motion (e.g., an acceleration of a body part measured by an accelerometer mounted to the body part), a signal of a natural or artificial process, or some other signal of interest that contains an oscillating pattern whose frequency could be determined.

It should be understood that the above embodiments, and other embodiments described herein, are provided for explanatory purposes, and are not intended to be limiting.

II. DETECTION OF PULSE RATES FROM DETECTED PHYSIOLOGICAL SIGNALS

A variety of signals or variables can include oscillating signals and/or other repeating patterns or events having a frequency or rate that can be determined and that is related to a property of interest. In a particular example, a cardiovascular pulse rate could be determined based on a plurality of detected samples of a physiological parameter related to the cardiovascular pulse rate, e.g., an electric current or potential in a body (e.g., an electrocardiogram (ECG)), or a volume, flow rate, pressure, or other properties of blood in a portion of vasculature (e.g., a volume of blood in a portion of subsurface vasculature in a wrist of a body). Such a physiological parameter could be detected by a wearable device, e.g., a wrist-mountable device that includes one or more sensors configured to detect the physiological parameter (e.g., by illuminating a portion of subsurface vasculature and detecting a volume of blood in the portion of subsurface vasculature based on a detected intensity of light that is responsively emitted from the portion of subsurface vasculature). Such a wearable device could then determine, using methods described herein, a pulse rate or other frequency information based on a plurality of detected samples of the physiological signal.

A detected signal containing an oscillating pattern of interest (e.g., a pattern related to a cardiovascular pulse) could include other contents, e.g., noise or artifact signals that are unrelated to the oscillating pattern. For example, the detected signal could include motion artefacts related to relative motion of a sensor and the course of the detected signal (e.g., a portion of subsurface vasculature), environmental noise (e.g., changes in a detected light intensity signal related to changes in ambient illumination), or other signals. Additionally or alternatively, noise or other undesirable aspects of a detected signal could be related to the means used to detect the signal, e.g., a photodiode dark current or shot noise, an amplifier noise characteristic, or some other source of unwanted (e.g., noise) signals. A method to detect the frequency of the oscillating pattern (e.g., to detect a cardiovascular pulse) can be configured to account for such confounding signals. Further, such a method could be configured to provide estimates of the frequency or rate (e.g., a cardiovascular pulse rate) having a specified frequency resolution (e.g., a determined pulse rate frequency resolution that is less than approximately 1 beat per minute) and/or temporal resolution (e.g., to provide estimates of a cardiovascular pulse rate for a plurality of samples of a detected signal at a spacing less than approximately 1 second, or preferentially at a spacing less than approximately 20 milliseconds).

An example of such a detected signal containing an oscillating pattern is illustrated in FIG. 1A. FIG. 1A shows an example detected light intensity signal 110 that could be detected using a photoplethysmographic sensor that is configured to illuminate blood in a portion of subsurface vasculature and to detect an intensity of responsively emitted light (e.g., light reflected, refracted, scattered, or otherwise emitted from the portion of subsurface vasculature and proximate other tissues). The detected light intensity signal 110 is composed of a plurality of samples generated by the photoplethysmographic sensor and includes a plurality of repeated patterns (e.g., approximately triangular pulses) related to the absorption of blood in the portion of subsurface vasculature over time. A cardiovascular pulse rate could be determined based on a number of the repeated patterns per period of time, an interval of time between one or more of the repeated patterns, or according to some other method. A shown in FIG. 110, the repeated patterns vary relative to each other; these variations could be related to changes over time of a cardiovascular pulse rate, a change of the pressure and/or volume generated by a heart over time, a motion artifact, a change in properties (e.g., stiffness) of the portion of subsurface vasculature, a change in the orientation of configuration of the body (e.g., a movement and/or raising of an arm containing the portion of subsurface vasculature), or some other processes or properties of a body.

A detected signal includes frequency content that could be detected, determined, and/or represented as a frequency spectrum. Such a frequency spectrum could include a plurality of frequency components (e.g., Fourier transform coefficients) having respective magnitudes and corresponding to contents of the detected signal at respective corresponding frequencies. Such a frequency spectrum could include peaks or other features related to an oscillating pattern (e.g., a repeating pattern related to a cardiovascular pulse) in the detected signal and having properties (e.g., center frequencies, widths, magnitudes, frequencies at maximum) related to corresponding properties of the oscillating pattern. Such features could be used to determine a rate or frequency of the oscillating pattern or other repeating pattern in the detected signal.

Figure 1B:
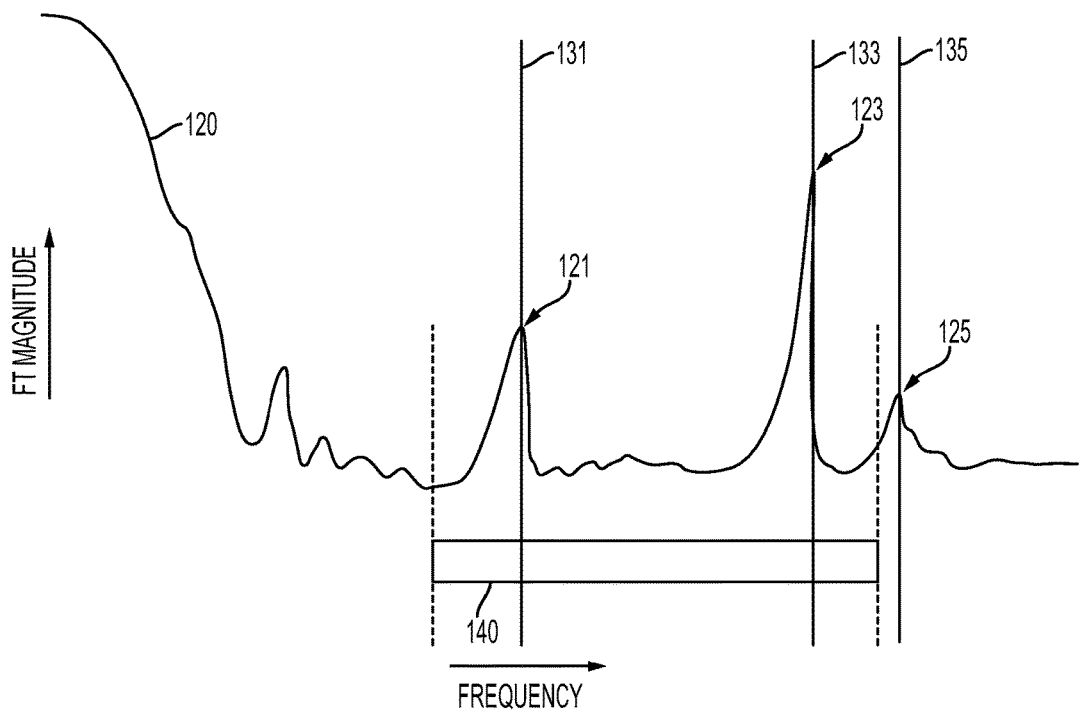
FIG. 1B is an example of a frequency spectrum of the detected signal depicted in FIG. 1A.

As an illustrative example, FIG. 1B shows a frequency spectrum 120 of the detected light intensity signal 110. The frequency spectrum includes first 121, second 123, and third 125 peaks at respective first 131, second 133, and third 135 frequencies (e.g., respective frequencies of the maximum of each of the peaks). These frequencies 131, 133, 135 could be related to the frequency of contents of the detected light intensity signal 110. For example, the frequency 131 of the first peak 121 in the frequency spectrum 120 could correspond to the frequency of the repeating pattern in the detected light intensity signal 110 and thus could be determined to determine a cardiovascular pulse rate. Other peaks or other features of the frequency spectrum 120 could be related to other contents of the detected light intensity signal 110, e.g., to noise signals (e.g., an oscillating signal coupled to a detector by mains power in an environment, an oscillating signal related to a steady gait or other repeated motion or action) or other oscillating or otherwise repeating contents of the signal (e.g., an oscillation in the detected signal 110 that is related to respiration). For example, the third peak 125 could be related to a harmonic of the repeating pattern in the detected light intensity signal 110 such that the third frequency 135 is approximately an integer multiple of the first frequency 131 (e.g., approximately twice the first frequency 131).

A frequency of a cardiovascular pulse (or some other repeating pattern or signal) in a detected signal (e.g., 110) could be determined in a variety of ways. In some examples, the frequency spectrum (e.g., 120) of the detected signal could be determined based on the plurality of samples of the signal and the cardiovascular pulse could be detected based on one or more determined features or properties of the frequency spectrum.

Such a frequency spectrum (e.g., 120) could be determined in a variety of ways. In some examples, a discrete Fourier transform (e.g., a fast Fourier transform) could be performed based on the plurality of samples (or a subset thereof, e.g., a set of samples of the plurality of samples that correspond to points in time within a specified range of times, e.g., a ten second window of time). In some examples, only a subset of a frequency spectrum could be determined (e.g., a subset of the frequency components of the frequency spectrum could be determined). For example, only those frequency components of the example spectrum 120 that are within the indicated range of frequencies 140 could be determined. In some examples, such a range of frequencies could be specified related to an expected range of values of the cardiovascular pulse (or other repeating pattern or event of interest), e.g., the range of frequencies could be between approximately 0.5 Hertz and approximately 3.5 Hertz (i.e., between approximately 30 beats per minute (BPM)) and approximately 200 BPM). Determining only a subset of the frequency components of a frequency spectrum could include performing steps of the Goertzel algorithm. In some examples, a first frequency spectrum could be available for a first set of the plurality of samples of the detected signal that is overlapping with a second set of the plurality of samples and a frequency spectrum for the second set of the plurality of samples could be determined by updating the first frequency spectrum based on those samples of the first and second sets of samples that are not overlapping (i.e., that are not in common between the sets of samples), e.g., using the sliding discrete Fourier transform.

Additionally or alternatively, a frequency of a cardiovascular pulse (or some other repeating pattern or signal) in a detected signal (e.g., 110) could be determined using time-domain methods. For example, a detected signal could be compared to a specified threshold value and a frequency of rising and/or falling transitions of the detected signal across the specified threshold could be determined and used to determine the cardiovascular pulse. In some examples, a template of a repeating pattern and/or of a cycle of an oscillating pattern could be compared to the detected signal (e.g., convolved) and used to determine a number, timing, interval between, and/or frequency of the repeating pattern.

In some examples, a digital phase-locked loop (PLL) could be operated on a set of samples of a detected signal in order to determine a frequency of contents of the repeating signal. Such a digital PLL could include a digital phase detector, low-pass filter, controlled-frequency oscillator, or other digital elements such that the digital PLL generates an oscillating signal. Such a PLL could include one or more specified parameters, e.g., a free-running frequency, an initial output frequency or other initial condition(s), an order, a capture range, a loop bandwidth, a steady-state error, or some other operational parameters. A digital PLL could be implemented in hardware (e.g., a plurality of logic gates of an application-specific integrated circuit, gates of a field-programmable gate array, or some other digital hardware components) and/or in software (e.g., implemented as a set of instructions that could be performed by a processor or controller to generate an oscillating signal based on an input plurality of samples of a signal).

Figure 2A:
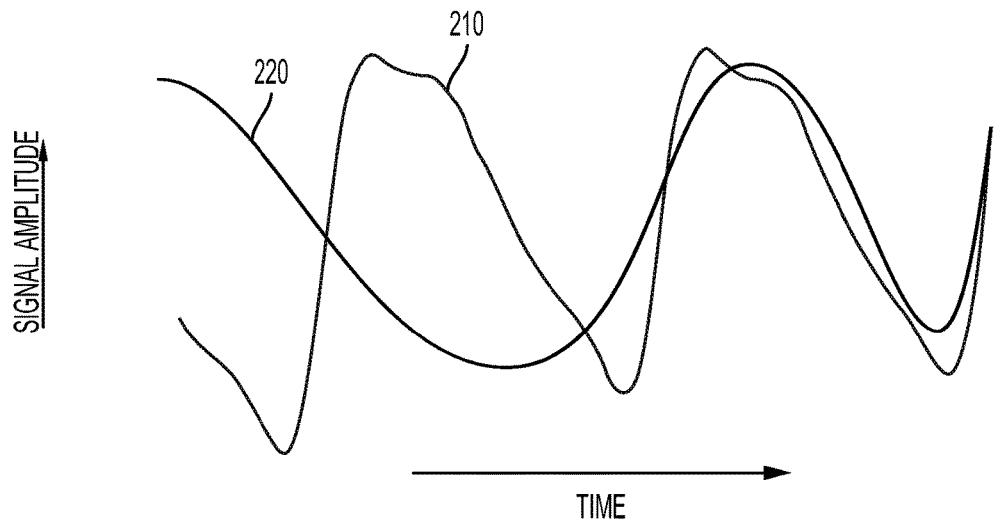
FIG. 2A is an example of a detected signal and an example oscillating signal generated by a phase-locked loop.

Such a digital PLL could be configured and/or operated based on the plurality of samples of the detected signal such that a frequency of the generated oscillating signal 'locks in' to the frequency of the repeating and/or oscillating content of the detected signal. As an illustrative example, FIG. 2A illustrates a set of samples of an example detected signal 210 (e.g., a detected photoplethysmographic signal from a portion of subsurface vasculature) that includes a repeating pattern having a frequency related to a cardiovascular pulse. An oscillating signal 220 generated by a digital PLL as described herein based on the samples of the detected signal 210 is shown overlaid on the detected signal 210. As shown in FIG. 2A, the digital PLL generates the oscillating signal 220 such that a frequency of the oscillating signal 220 'locks in' to (i.e., becomes more similar in value to) a frequency of oscillating content in the detected signal 210 (i.e., the frequency of the oscillating signal 220 is, at the end of the generated oscillating signal 220, approximately equal to the frequency of oscillating content in the detected signal 210).

Note that the oscillating signal 220 shown in FIG. 2A is meant as a non-limiting example. Different digital PLLs (e.g., digital PLLs having different operational parameters, e.g., different initial frequencies) could be operated to generate different oscillating signals from the illustrated oscillating signal 220. Further, frequencies of such different generated oscillating signals could 'lock in' to and/or have values at the end of the generated oscillating signals could differ from each other. In some examples, the frequency of such a generated oscillating signal could, at the end of the generated oscillating signal, have a value that is substantially different from the frequency of oscillating content in the detected signal 210. This could be related to a level of noise in the detected signal, an initial condition and/or operational parameter of a corresponding digital PLL (e.g., an initial frequency that has a value too far from the frequency of the oscillating content and/or an adaptation rate and/or lowpass filter cutoff frequency that are too low), the presence of harmonics of the oscillating content in the detected signal, or some other factors. As a result, a frequency of an oscillating signal generated by a digital PLL could be inaccurate relative to the frequency of oscillating content of a corresponding detected signal.

In some examples, a plurality of digital PLLs could be operated, based on a detected signal, to generate respective oscillating signals and a plurality of frequencies of the generated oscillating signals (e.g., instantaneous frequencies of the generated oscillating signals at the ends of the oscillating signals) could be determined and used to determine a frequency or rate (e.g., a cardiovascular pulse rate) of oscillating and/or repeating contents of the detected signal (e.g., an oscillating waveform in a detected intensity of light that is related to a cardiovascular pulse). Digital PLLs of such a plurality of digital PLLs could have respective different operational parameters (e.g., initial frequencies, lowpass filter coefficients, tracking rates) such that oscillating signals generated by the plurality of digital PLLs are not identical. The detected signal could be compared to each of the generated oscillating signals (e.g., by determining a correlation) and a subset of the generated oscillating signals could be selected based on the comparison (e.g., the half of the generated oscillating signals having the highest determined correlations with the detected signal could be selected). A frequency of each of the selected generated oscillating signals could then be determined (e.g., based on an internal state, e.g., a final frequency of a controlled-frequency oscillator, of corresponding digital PLLs) and used (e.g., by determining an average of the frequencies) to determine a frequency or rate (e.g., a cardiovascular pulse rate) of oscillating and/or repeating contents of the detected signal.

Figure 2B:
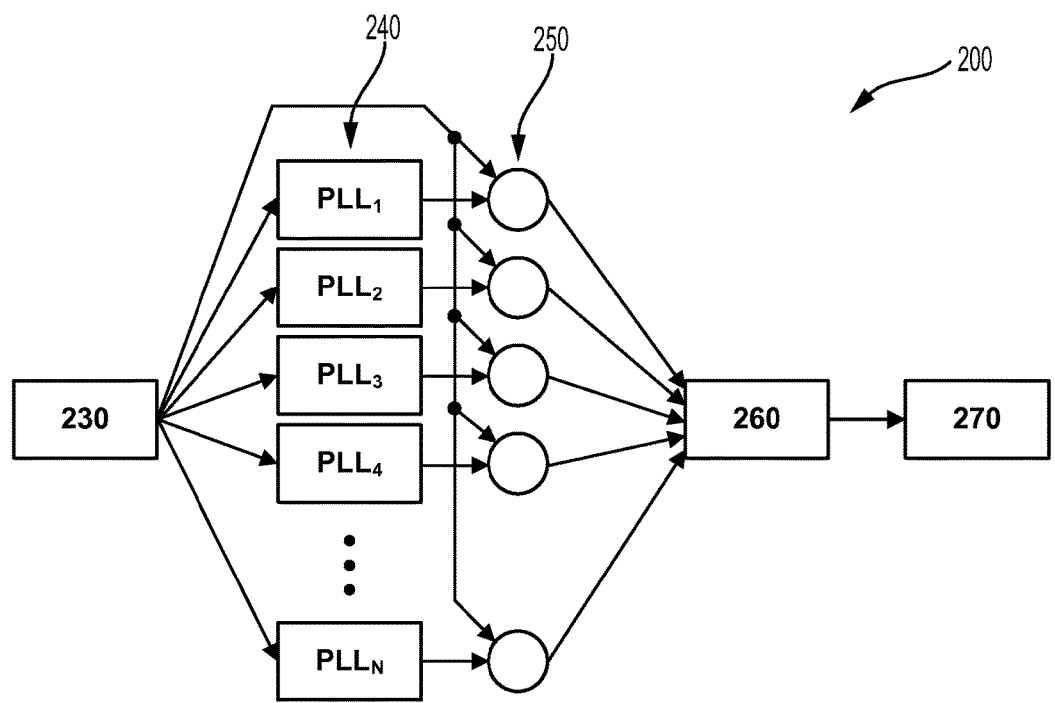
FIG. 2B is a diagram of an example system configured to determine a pulse rate.

To illustrate the use of a plurality of digital PLLs to determine a cardiovascular pulse rate or other frequency of a detected signal, FIG. 2B illustrates a system 200 that could be operated to determine a cardiovascular pulse rate. The system 200 includes a sensor 230 configured to obtain a plurality of samples of an input signal (e.g., to optically detect a blood volume signal, as described elsewhere herein) that is related to a cardiovascular pulse. The system 200 additionally includes a plurality of digital phase-locked loops 240 configured to generate respective oscillating signals based on the plurality of samples generated by the sensor 230. Each of the digital PLLs 240 has a different set of respective operational parameters (e.g., free-running frequency, initial states, adaptation rate, loop bandwidth). The system 200 additionally includes a plurality of similarity-determining elements 250 configured to compare the plurality of samples obtained by the sensor 230 to samples of each of the oscillating signals generated by the plurality of digital PLLs 240. The system additionally includes a selection and combination element 260 configured to select a number of the oscillating signals generated by the digital PLLs 240 based on the comparisons and to combine frequencies of the generated oscillating signals (determined, e.g., based on an internal state of respective digital PLLs of the plurality of digital PLLs 240) to generate a cardiovascular pulse rate. The system further includes an output 270 configured to receive the determined cardiovascular pulse rate and to operate based on the received cardiovascular pulse rate, e.g., to indicate the pulse rate to a user (e.g., using a display of the system), to indicate the pulse rate to an external system (e.g., using a radio or other communications interface), to store the pulse rate (e.g., using a memory), or to perform some other operations.

The plurality of similarity-determining elements 250 could compare the plurality of samples obtained by the sensor 230 to samples of each of the oscillating signals generated by the plurality of digital PLLs 240 using a variety of methods. For example, the plurality of similarity-determining elements 250 could determine a correlation (e.g., a Pearson product-moment correlation coefficient), a sum of squared differences, a sum of differences, a weighted sum of squared differences, a product of differences, a product of squared differences or some other determination, a function of such determinations (e.g., a nonlinear function of a sum of squared differences), and/or combination of determinations. The similarity-determining elements 250 could compare all of the plurality of samples obtained by the sensor 230 to corresponding samples of each of the oscillating signals generated by the plurality of digital PLLs 240. Alternatively, the similarity-determining elements 250 could compare a subset of the obtained samples (e.g., the final 10% of samples generated by the sensor 230) to corresponding samples of each of the oscillating signals generated by the plurality of digital PLLs 240 (e.g., to compare the outputs of the PLLs 240 during latter samples of the obtained plurality of samples, when some or all of the PLLs 240 have 'locked in' to any oscillating content of the plurality of obtained samples).

The selection and combination element 260 could be configured to select a number of the oscillating signals generated by the digital PLLs 240 in a variety of ways. In some examples, the selection and combination element 260 could select a specified number of the oscillating signals, e.g., could select the specified number of the most similar oscillating signals (e.g., the oscillating signals corresponding to the highest determined correlation coefficients). Alternatively, the selection and combination element 260 could select any oscillating signals that correspond to measures of similarity (e.g., correlation coefficients) that are greater than a specified value (e.g., determined correlation coefficients greater than a specified value). The selection and combination element 260 could be configured select a specified or variable number of the generated oscillating signals according to some other method.

The selection and combination element 260 could be configured to combine frequencies of selected generated oscillating signals to generate a cardiovascular pulse rate in a variety of ways. In some examples, the selection and combination element 260 could determine an average (e.g., a linear average, a geometric average) of the determined frequencies. In some examples, the selection and combination element 260 could determine a weighted average or other combination of the determined frequencies, e.g., weighting the determined frequencies according to corresponding determined measures of similarity (e.g., such that a determined pulse rate is weighted toward frequencies corresponding to generated oscillating signals that are more similar to the plurality of samples of the detected signal). The selection and combination element 260 could be configured to combine frequencies of selected generated oscillating signals to generate a cardiovascular pulse rate according to some other method.

Note that one or more elements of the system 200 (e.g., the plurality of digital phase-locked loops 240, the plurality of similarity-determining elements 250, the selection and combination element 260) could be implemented in hardware (e.g., a plurality of logic gates of an application-specific integrated circuit, gates of a field-programmable gate array, or some other digital hardware components) and/or in software (e.g., implemented as a set of instructions that could be performed by a processor or controller to generate an oscillating signal based on an input plurality of samples of a signal). Further, one or more elements of the system 200 could be implemented in a body-mountable device (e.g., the sensor 230, a display or other user interface element(s) of the output 270) and other elements of the system 200 (e.g., the plurality of digital phase-locked loops 240, the plurality of similarity-determining elements 250, the selection and combination element 260) could be implemented in a server, cellphone, cloud computing service, or other system(s) in communication with the body-mountable device. For example, the sensor 230 could be part of a wrist-mountable device in communication with a server on which are implemented the plurality of digital phase-locked loops 240, the plurality of similarity-determining elements 250, and the selection and combination element 260. The wrist-mountable device could transmit samples of a photoplethysmographic signal or other signal related to a cardiovascular pulse to the server, and the server could determine a cardiovascular pulse rate based on the received samples. Such a distribution of elements of the system 200 could be related to a power budget, an amount of memory (e.g., random-access memory of a controller), or some other property of the wrist-mountable device.

In some examples, two or more cardiovascular pulse rates (or other frequencies or rates) determined using respective two or more different systems or methods described herein could be combined to generate an improved estimate of the cardiovascular pulse rate. For example, a cardiovascular pulse rate determined using a first method (e.g., a method including the operation of a plurality of digital phase locked loops based on obtained samples of a signal and combining a set of frequencies of oscillating signals generated by the digital phase locked loops) could have first properties (e.g., a high accuracy, a high stability over time, a low frequency resolution) and a second cardiovascular pulse rate determined using a second method (e.g., a method including determining a frequency spectrum of the obtained samples of the signal and determining a frequency of a feature of the frequency spectrum) could have second properties (e.g., a low accuracy, a low stability over time, a high frequency resolution). The results (e.g., determined cardiovascular pulse rates) of the first and second (or more) methods could be combined (e.g., averaged, weighted averaged, applied to a neural network) to generate an estimated cardiovascular pulse rate that has properties that are improved relative to the properties of the first and second (or more) determined cardiovascular pulse rate used to generate the estimated cardiovascular pulse rate. For example, the first and second determined cardiovascular pulse rate could be combined to produce an estimated cardiovascular pulse rate that has a high accuracy, a high stability over time, and a high frequency resolution.

Additionally or alternatively, two or more of the methods described herein could be combined to form a hybrid method for determining a cardiovascular pulse rate. For example, a cardiovascular pulse rate determined based on the operation of a plurality of PLLs (e.g., using the system 200 illustrated in FIG. 2B) could be used to select a peak or other feature in a corresponding frequency spectrum, and a higher-resolution (or otherwise improved) cardiovascular pulse rate could be determined based on the selected peak (e.g., based on a frequency of the frequency component of the peak that has the highest magnitude).

Figure 3:
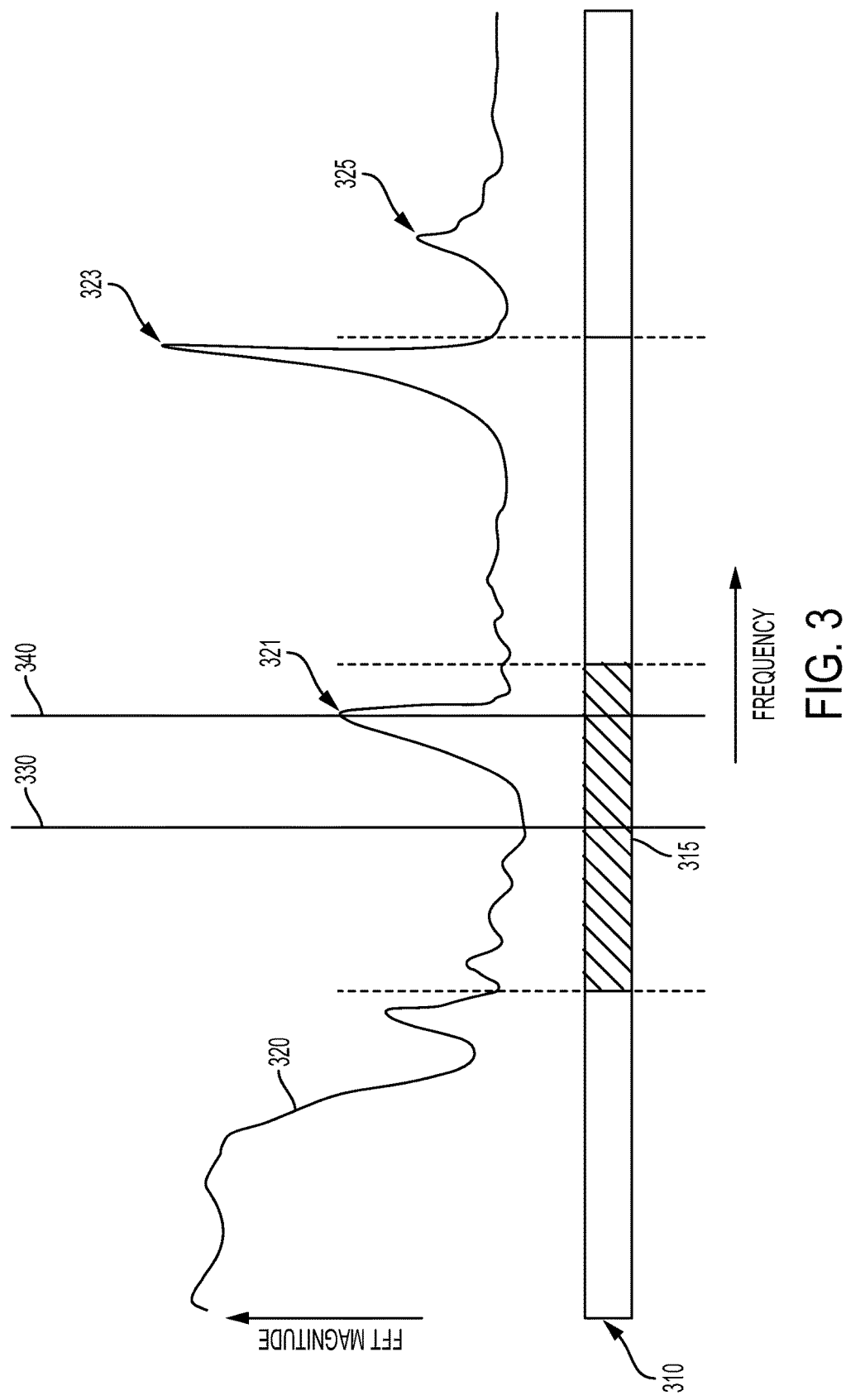
FIG. 3 is an example of a frequency spectrum of a detected signal that contains an oscillating pattern.

To illustrate this method, FIG. 3 shows a frequency spectrum 320 determined based on a plurality of samples of a detected signal (e.g., a detected tonographic signal, photoplethysmographic signal, or other physiological parameter) related to a cardiovascular pulse. The frequency spectrum 320 includes first 321, second 323, and third 325 peaks. These frequencies 231, 233, 235 could be related to the frequency of contents of the detected signal (e.g., to contents of the detected signal related to the cardiovascular pulse). For example, the frequency 340 of the first peak 321 in the frequency spectrum 120 could correspond to the frequency of the cardiovascular pulse and thus could be determined to determine a cardiovascular pulse rate. Other peaks or other features of the frequency spectrum 320 could be related to other contents of the detected signal, e.g., to noise signals or other oscillating or otherwise repeating contents of the signal.

The frequency ranges 310 illustrated beneath the determined frequency spectrum 320 illustrate the frequency resolution of a system configured to operate a plurality of digital PLLs to generate respective oscillating signals based on the plurality of samples of the detected signal and to determine a cardiovascular pulse rate based on frequencies of the generated oscillating signals (e.g., a system similar to system 200). For example, the system could be configured to output a cardiovascular pulse rate that is equal to a center frequency of one of the illustrated frequency ranges. Thus, such a system outputting the illustrated frequency 330 could indicate that the true value of the cardiovascular pulse rate is within the corresponding illustrated frequency range 315. The output of such a system could be used to select a peak of the frequency spectrum 320 or to otherwise determine a cardiovascular pulse rate based on the frequency spectrum 320. For example, a maximum of the determined frequency spectrum 320 could be determined within a specified range of frequencies of the illustrated determined frequency 330 (e.g., within a range of frequencies indicated by the illustrated frequency range 315). Such of combination of multiple methods for cardiovascular pulse rate estimation could prevent an erroneous cardiovascular pulse rate from being determined, e.g., a rate corresponding to the second peak 323 if only the maximum of the determined frequency spectrum 320 is determined without consideration of the illustrated 330 frequency determined based on the operation of the plurality of digital PLLs.

In some examples, a frequency resolution of a frequency spectrum that is determined based on a plurality of samples of a detected signal could be increased. This could include zero-padding the plurality of samples (i.e., appending a plurality of zeros to the plurality of samples before determining the frequency spectrum). Alternatively, a frequency spectrum could be interpolated using a linear interpolation, a biquadratic interpolation, a sinc interpolation, a nearest neighbor interpolation, a spline interpolation, or some other means to generate a plurality additional frequency components corresponding to respective frequencies between the frequencies corresponding to the frequency components of the frequency spectrum.

In a preferred embodiment, a frequency of a local maximum of a frequency spectrum could be determined (e.g., a global maximum of the frequency spectrum, a maximum within a range of frequencies based on a frequency determined based on the operation of a plurality of digital PLLs) and frequency components corresponding to frequencies within a specified range of the determined local maximum frequency could be interpolated based on a sinc function. For example, a sinc interpolation could be performed based on a first frequency component corresponding to the determined frequency (e.g., a frequency component having a global or local maximum magnitude within the frequency spectrum) and a set of other frequency components of the frequency spectrum that are proximate (e.g., corresponding to nearby frequencies) the first frequency component. For example, the sinc interpolation could be performed based on the first frequency component and a certain number of other frequency components that are proximate the first frequency component. An updated estimate of the local maximum of a frequency spectrum could be determined based on the generated interpolated frequency components, e.g., based on a maximum magnitude frequency component of the interpolated frequency components. Additionally or alternatively, a frequency estimate determined from a frequency spectrum could have an increased frequency resolution provided by some other method, e.g., by fitting a curve or parameterized function to frequency components of the frequency spectrum and determining a property (e.g., a center frequency, a frequency of a maximum) of the fitted curve or parameterized function.

A variety of physiological or other signals related to a cardiovascular pulse or to some other oscillating or otherwise repeating pattern could be detected and used to determine a cardiovascular pulse rate or other frequency or rate as described herein. In some examples, such samples of such signals could be detected using sensors disposed in a body-mounted device. In such examples, a cardiovascular pulse rate could be determined at a plurality of points in time (e.g., once per second) over a protracted period of time (e.g., several days, several weeks). Such high temporal resolution detection of cardiovascular pulse rate could provide for the detection of health states (e.g., arrhythmias, heart disease, heart attacks, orthostatic hypotension) of a person, for the determination of information related to physical activity (e.g., information related to cardiovascular function during exercise that could be used, e.g., to plan a training regimen), or to determine some other information. Detection of cardiovascular pulse rate over a protracted period of time could permit the detection of information related to infrequent events (e.g., infrequent episodes of arrhythmia), the determination of baselines or other information about cardiovascular function over a protracted period of time (e.g., baselines of cardiovascular function related to the time of day), or the determination of other information.

Physiological parameters or other physical variables that are related to a cardiovascular pulse could include electrical potentials or currents related to the activity of the heart, pressures and/or displacements related to changes in the volume and/or pressure of blood in portions of subsurface vasculature, the flow rate, volume, pressure, or other properties of blood in portions of subsurface vasculature, or some other detectable parameters. Such parameters could be detected (e.g., by a sensor 230) electrically (e.g., using two or more electrodes in electrical contact with respective portions of skin), ultrasonically (e.g., emitting ultrasonic energy into blood in a portion of vasculature and detecting reflected ultrasonic energy having a property (e.g., a change in frequency) related to a flow velocity of blood), tonometrically (e.g., by detecting a pressure and/or displacement at a skin surface related to the pressure and/or volume of blood), optically (e.g., by emitting light (e.g., coherent light) into a portion of subsurface vasculature and detecting a property (e.g., an intensity, a pattern of constructive and destructive interference) of responsively emitted light), or through some other means.

In a preferred embodiment, a signal related to the volume of blood in a portion of subsurface vasculature could be detected by illuminating the portion of subsurface vasculature and detecting light emitted from the portion of subsurface vasculature in response to the illumination. Such a signal could be detected and/or samples at a plurality of points in time to provide a plurality of samples of the detected signal (e.g., at a rate of approximately 50 Hertz). Properties of the emitted light could be specified such that the emitted light can penetrate a person's skin into the portion of subsurface vasculature, for example, into a lumen of the subsurface vasculature. The transmitted illumination can be any kind of illumination that is benign to the wearer and that results at least in an amount of absorption by blood in the subsurface vasculature that is related to the volume of the blood in the subsurface vasculature, e.g., such that light responsively emitted from the body has one or more detectable properties related to the volume of flow and/or the pulse rate of blood in the portion of subsurface vasculature (e.g., an intensity related to the amount of blood in the portion of subsurface vasculature).

The wavelength of the transmitted illumination could be specified to penetrate biological tissues of a body; for example, the transmitted illumination could have a wavelength within a near-infrared (NIR) transparency window of biological tissue (e.g., between approximately 650 nanometers and approximately 950 nanometers and/or between approximately 1000 nanometers and approximately 1350 nanometers). The wavelength of the transmitted illumination could be specified to be a wavelength that is absorbed and/or scattered by blood cells. The wavelength of the transmitted illumination could be between approximately 400 nanometers and approximately 1000 nanometers. Further, multiple wavelengths of light could be emitted and properties of respective lights responsively emitted from the portion of subsurface vasculature could be detected to provide some additional information, e.g., information about the absorption spectrum of the blood that could be used to determine an oxygen saturation or level of oxygenation of the blood.

Note that the detected signals 110, 210, frequency spectra 120, 320, generated oscillating signal 220, and other example signals illustrated in FIGS. 1A, 1B, 2A, 3, and elsewhere herein are non-limiting examples intended to illustrate a variety of properties of signals related to a cardiovascular pulse (or other oscillating patterns in a signal of interest) and to methods that could be used to determine a cardiovascular pulse rate based on detected properties of such detected signals and/or properties (e.g., features) of corresponding frequency spectra. Such methods could be applied to a variety of different detected signals (e.g., light intensities related to a volume of blood in a portion of subsurface vasculature) to determine a frequency or rate of an oscillating pattern or other repeating feature in such detected signals (e.g., a cardiovascular pulse rate). Techniques and systems as described herein could be applied to determine a frequency or rate of a variety of different oscillating or repeating patterns, waveforms, or features in a variety of different detected signals related to a variety of different physical, mathematical, chemical, economical, sociological, and/or physiological parameters. Additional methods for determining a cardiovascular pulse rate based on a plurality of samples of a photoplethysmographic, ECG, tonometric, or other detected physiological signal are anticipated.

Further, note that descriptions of the determination of cardiovascular pulse rates based on samples of detected signals using methods herein are intended as non-limiting illustrative examples of the determination of frequencies and/or rates of oscillating and/or repeating contents of a variety of detected signals. Such methods could be used to determine a rate of breathing, a rate of locomotion or other repeated action or motion, or some other rate or frequency that could be determined based on a detected physiological or other signal (e.g., a strain detected using a chest strap breathing sensor, an accelerometer mounted to a body part). Further, systems and methods described herein could be used to determine frequencies or rates of such processes in an animal. Systems and methods described herein could be used to determine frequencies or rates of contents of signals detected from a natural environment (e.g., a frequency of cyclical water flows in a marsh, lake or stream), an artificial environment (e.g., a frequency of repeating patterns in a detected rate of inflow into a water treatment process), or some other environment of interest.

III. DETERMINATION OF PULSE RATES FOR A PLURALITY OF PERIODS OF TIME

A cardiovascular pulse rate (or a frequency or rate of some other repeating process) could be determined at a plurality of points in time (e.g., based on respectively sets of a plurality of a detected signal related to the cardiovascular pulse) according to an application. In some examples, such a plurality of determined cardiovascular pulse rates could be used to detect health states or conditions of a person, e.g., to detect an arrhythmia, to detect a baseline pulse rate, to detect a baseline pulse rate variability, or to determine some other information. Additionally or alternatively, the determination of a plurality of cardiovascular pulse rates could provide for improvement of the determined cardiovascular pulse rates, e.g., by applying a filter to the determined rates to remove noise from the determined rates, to increase an accuracy of the determined rates, to prevent an erroneous rate from being determined (e.g., a rate related to a harmonic of a cardiovascular pulse rate, a rate related to noise content in a detected signal), or to otherwise improve the determined cardiovascular pulse rates.

In some examples, individual determined pulse rates of such a plurality of determined pulse rates could be based on respective overlapping sets of samples of a detected signal. That is, a plurality of samples of a signal relating to the cardiovascular pulse could be partitioned into overlapping subsets and a cardiovascular pulse rate could be determined based on each of the subsets of the plurality of samples. This could be done, e.g., to provide a high rate and/or temporal resolution of the determined cardiovascular pulse rates while using a method that requires an amount of samples corresponding to a time period that is longer that the rate of the determined cardiovascular pulse rates. For example, determination of cardiovascular pulse rates having a specified frequency resolution (e.g., approximately 0.5 Hertz, i.e., approximately 6 beats per minute) could require samples of a detected signal that span a specified time period (e.g., approximately 10 seconds) that is longer than a specified rate at which the cardiovascular pulse rates are generated (e.g., a rate of approximately 1 Hertz).

Figure 4:
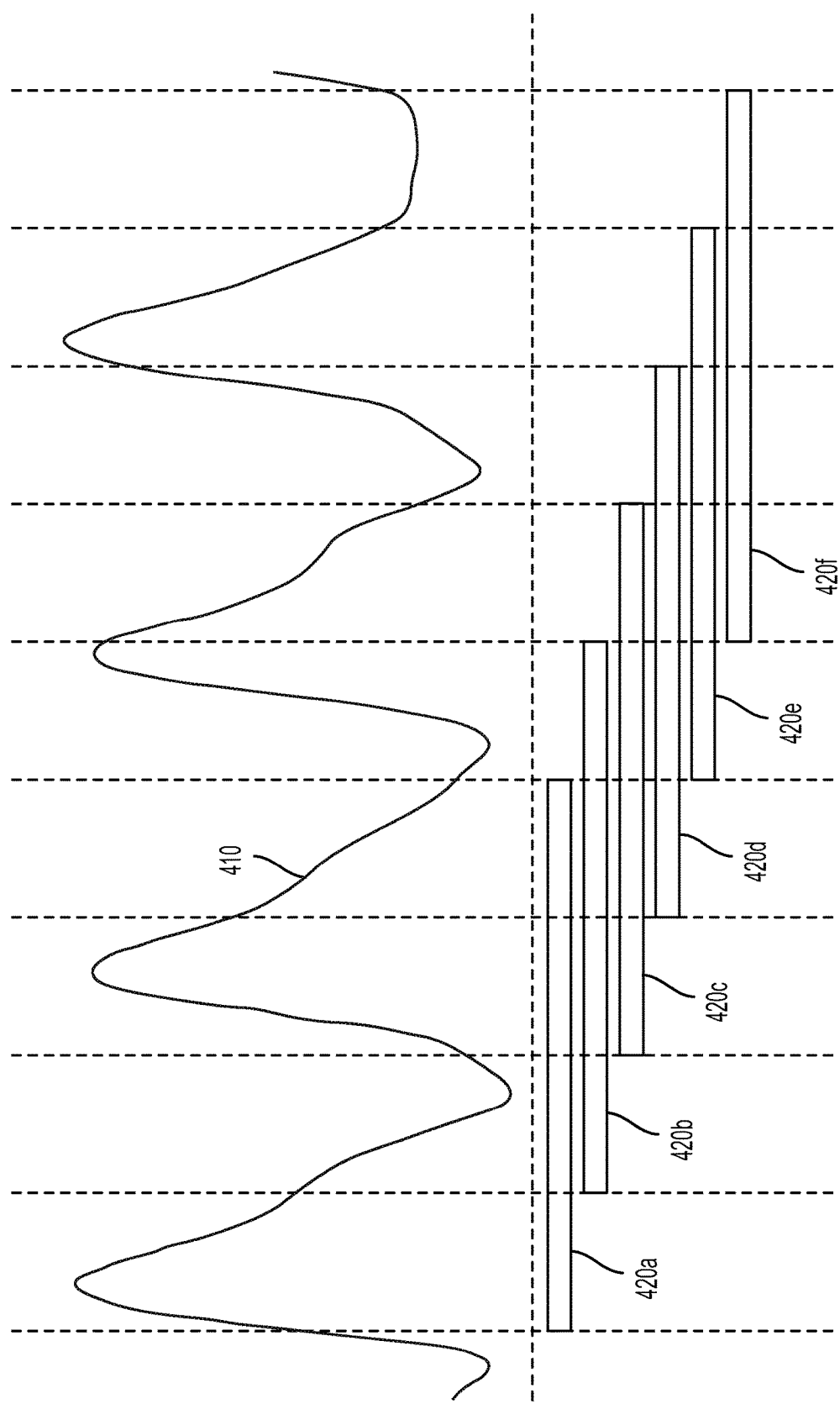
FIG. 4 illustrates a number of example partitions of samples of an example detected signal.

FIG. 4 illustrates an example detected light intensity signal 410 that could be detected using a photoplethysmographic sensor that is configured to illuminate blood in a portion of subsurface vasculature and to detect an intensity of responsively emitted light (e.g., light reflected, refracted, scattered, or otherwise emitted from the portion of subsurface vasculature and proximate other tissues). The detected light intensity signal 410 is composed of a plurality of samples generated by the photoplethysmographic sensor and includes a plurality of repeated patterns (e.g., approximately triangular pulses) related to the absorption of blood in the portion of subsurface vasculature over time. A plurality of overlapping time periods 420a-f illustrate time periods corresponding to overlapping sets of samples of the detected signal 410 into which the plurality of samples of the detected signal 410 could be partitioned. A cardiovascular pulse rate could be determined for each of the overlapping time periods 420a-f based on respective overlapping subsets of the samples of the detected signal 410.

Note that the illustrated degree of overlap of the illustrated overlapping time periods 420a-f and corresponding degree of overlap of corresponding subsets of samples of the detected signal 410 is intended as a non-limiting example. A plurality of samples of a detected signal could be partitioned into overlapping subsets of samples that have greater or lesser amounts of overlap according to an application (e.g., an overlap of approximate 1 second such that cardiovascular pulse rates could be determined at a rate of 1 Hertz). In a particular example, a plurality of samples of a detected signal could be partitioned into overlapping subsets of samples such that neighboring subsets of samples overlap by all but one sample, respectively. That is, a first subset of samples could include a first unshared sample followed by a plurality of shared samples and a second subset of samples could include the plurality of shared samples followed by a second unshared sample. In such an example, cardiovascular pulse rates could be determined at the same rate as samples of the detected signal are obtained, e.g., each additional obtained sample could be used to update a previously determined cardiovascular pulse rate and/or to otherwise generate a new determined cardiovascular pulse rate based on each additional obtained sample.

A plurality of cardiovascular pulse rates determined based on a respective plurality of overlapping set of samples of a detected signal could be filtered or otherwise modified (i.e., a particular determined cardiovascular pulse rate could be modified based on one or more other determined cardiovascular pulse rates). This could include using a lowpass, highpass, bandpass, Wiener, or other kind of filter to the plurality of cardiovascular pulse rates.

In a preferred embodiment, a plurality of digital PLLs could be operated based on each overlapping subset of a plurality of samples of a detected signal to determine a cardiovascular pulse rate corresponding to each overlapping subset of samples. Such determined cardiovascular pulse rates could then be filtered using a bidirectional statistical filter, e.g., by applying the forward-backward algorithm. Such a bidirectional statistical filter could determine, for each subset of samples, a probability distribution (e.g., a probability mass function defined across a plurality of discrete possible values of a cardiovascular pulse rate) based on the cardiovascular pulse rates determined (e.g., by the operation of a plurality of digital PLLs) for prior and subsequent subsets of overlapping samples. This could include determining, for a particular subset of samples, for each of a discrete set of possible values of the cardiovascular pulse rate, the probability of observing a cardiovascular pulse rate having a particular value given cardiovascular pulse rates determined based on prior subsets of samples and further based on the probability of observing cardiovascular pulse rates determined based on subsequent subsets of samples assuming the particular value. Transition probabilities for such statistical filters could be determined based on a particular subset of samples of a detected signal, based on a plurality of cardiovascular pulse rates determined based on detected samples of a signal, determined based on a plurality of such detected signals (e.g., from a plurality of different individuals and/or from a plurality of periods of time from a particular individual), or determined according to some other consideration.

Further, in such examples (i.e., wherein a plurality of digital PLLs are operated based on each overlapping subset of a plurality of samples of a detected signal to determine a cardiovascular pulse rate corresponding to each overlapping subset of samples), operational parameters of the plurality of digital PLLs could be related to such detected cardiovascular pulse rates. For example, operational parameters (e.g., free-running frequencies, initial frequencies, initial states, lock-in ranges, or other operational parameters) of a plurality of digital PLLs operated based on a first subset of samples of a detected signal could be based on a cardiovascular pulse rate determined based on a second, prior subset of samples of a detected signal. For example, free-running frequencies of a plurality of digital PLLs operated based on a first subset of samples of a detected signal could be specified based on a cardiovascular pulse rate determined based on a second subset of the samples of the detected signal, e.g., could be set according to a range of values centered on the determined cardiovascular pulse rate for the second subset of samples.

In another preferred embodiment, a plurality of frequency spectra could be determined (e.g., using the discrete frequency transform) based on each overlapping subset of a plurality of samples of a detected signal to determine a cardiovascular pulse rate corresponding to each overlapping subset of samples (e.g., by determining a frequency of a peak or other local or global maximum of each of the frequency spectra). Such determined cardiovascular pulse rates could then be filtered by determining, for each determined cardiovascular pulse rate, a filtered cardiovascular pulse rate based on a combination of the determined cardiovascular pulse rate and one or more prior cardiovascular pulse rates. For example, a filtered cardiovascular pulse rate could be determined for a first cardiovascular pulse rate by determining a weighted combination of the first cardiovascular pulse rate and a second cardiovascular pulse rate corresponding to a subset of detected signal samples that are prior to an overlapping subset of detected signal samples corresponding to the first cardiovascular pulse rate. Such a weighted combination could be related to an estimate of the rate of change over time of the cardiovascular pulse. For example, the weighted combination could be determined according to the alpha-beta filter. That is, the filtered cardiovascular pulse rate could be determined based on a weighted combination of the first cardiovascular pulse rate and an estimate of the first cardiovascular pulse rate, wherein the estimate of the first cardiovascular pulse rate is based on the second cardiovascular pulse rate and an estimate of the rate of change over time of the cardiovascular pulse rate.

In some examples, determination of a filtered cardiovascular pulse rate based on a weighted combination of a first cardiovascular pulse rate corresponding to a first subset of detected signal samples and a second cardiovascular pulse rate corresponding to a second, prior subset of detected signal samples could include combining the first and second cardiovascular pulse rates based on a weighting factor that is related to a determined confidence level of the first determined cardiovascular pulse rate. For example, the first cardiovascular pulse rate could be determined based on the second cardiovascular pulse rate using the alpha-beta filter, where the adaptation rate (i.e., the 'alpha' parameter of the alpha-beta filter) is related to such a determined confidence level. Such a weighting factor could be applied to combine first and second cardiovascular pulse rates such that higher values of the determined confidence level result in the filtered cardiovascular pulse rate being more weighted toward the value of the first cardiovascular pulse rate. A determined confidence level as described herein could be determined in a variety of ways. For example, a confidence level of a particular determined cardiovascular pulse rate could be determined based on a magnitude of a local maximum of a frequency spectrum that is used to determine the particular determined cardiovascular pulse rate and on an overall energy in such a frequency spectrum. In a preferred embodiment, a confidence level could be determined based on a ratio of the squared magnitude of a frequency component of the frequency spectrum that corresponds to the local maximum and the sum of the squared magnitudes of the frequency components in the frequency spectrum.

In examples wherein a frequency spectrum is determined for each sample of a detected signal (i.e., wherein adjacent overlapping subsets of samples of the plurality of samples of the detected signal are shifted in time relative to each other by a single sample) or at some other high rate relative to the sample rate of the detected signal, a frequency spectrum of a first subset of samples could be determined based on a frequency spectrum determined for a second, overlapping, prior subset of samples. For example, a sliding discrete Fourier transform could be performed, based on a sample of a first subset of samples that is not in common with samples of a second, overlapping, prior subset of samples (e.g., the final sample of the first subset of samples), a sample of the second subset of samples that is not in common with the first subset of samples (e.g., the first samples of the second subset of samples), and a frequency spectrum determined for the second set of samples.

Further, in examples wherein only a specified range of frequencies are of interest, only those frequency components corresponding to frequencies within the specified range of frequencies could be determined. For example, when determining a cardiovascular pulse rate, only frequency components corresponding to physiologically possible cardiovascular pulse rates could be determined, e.g., those components corresponding to rates between approximately 0.5 Hertz and approximately 3.5 Hertz. This could include using the Goertzel algorithm to determine a set of discrete Fourier coefficients based on a plurality of samples. Alternatively, in examples wherein a first frequency spectrum for a first set of samples based on a second frequency spectrum determined for a second, overlapping, prior set of samples (e.g., by updating the second frequency spectrum using a sliding discrete Fourier transform), only those frequency components corresponding to frequencies within the specified range of frequencies could be determined and/or updated.

IV. REMOVAL OF NOISE FROM DETECTED SIGNALS RELATED TO PULSE RATE

Detected signals related to a cardiovascular pulse rate (or to some other oscillating pattern or otherwise repeating content of interest) could include components that are not related to the content of interest. For example, the detected signals could include environmental noise (e.g., signal components related to electromagnetic noise, changes in ambient illumination, or some other processes). The detected signals could also include contents related to changes in the configuration of the body (e.g., a change in perfusion level of tissue, a sympathetic response, contraction of a muscle) and/or of a system configured to detect the detected signals (e.g., motion of a photoplethysmographic sensor or other sensor of a body-mountable device relative to a portion of subsurface vasculature or other target). In some examples, a method or system for determining a cardiovascular pulse rate (or other rate or frequency of interest) from a detected signal could be configured to remove such unwanted content from the detected signal before determining the cardiovascular pulse rate, e.g., by applying a bandpass, Wiener, lowpass, or other frequency and/or time-domain filter to samples of the detected signal.

In some examples, a physiological parameter or other detectable property or variable in an environment could be related to unwanted content in the detected signal. For example, unwanted content of the detected signal could be related to relative motion between a sensor and sensed environment (e.g., between a photoplethysmographic sensor and a portion of subsurface vasculature). In such examples, the related physiological parameter or other detectable property could be detected to generate an artifact signal and the generated artifact signal (e.g., a plurality of samples of the artifact signal) could be used to wholly or partially filter or otherwise remove the related unwanted content (e.g., motion artifacts) from the detected signal. For example, an accelerometer could be configured to measure the motion (e.g., to measure the acceleration in one or more directions) of a sensor relative to a target environment (e.g., to detect the acceleration of a photoplethysmographic sensor of a body-mountable device, e.g., relative to a portion of subsurface vasculature) and an artifact signal generated by the accelerometer could be used to filter the signal detected by the sensor.

Filtering or otherwise modifying a detected signal based on an artifact signal could be performed in a variety of ways. In some examples, the artifact signal could be used to control an amplitude of the detected signal (e.g., by multiplying each sample of the detected signal by a multiple or other function of a corresponding sample of the artifact signal). Additionally or alternatively, the artifact signal could be subtracted from the detected signal. More complicated methods could be employed to combine the detected signal and the artifact signal, for example, convolution, applying the samples of the detected signal and the artifact signal to a multinomial function or lookup table, or some other method. Further, such methods could be employed based on a filtered version of the artifact signal, e.g., the artifact signal could be lowpass filtered, highpass filtered, or otherwise modified before being used to filter or otherwise modify the detected signal.

Figure 5A:
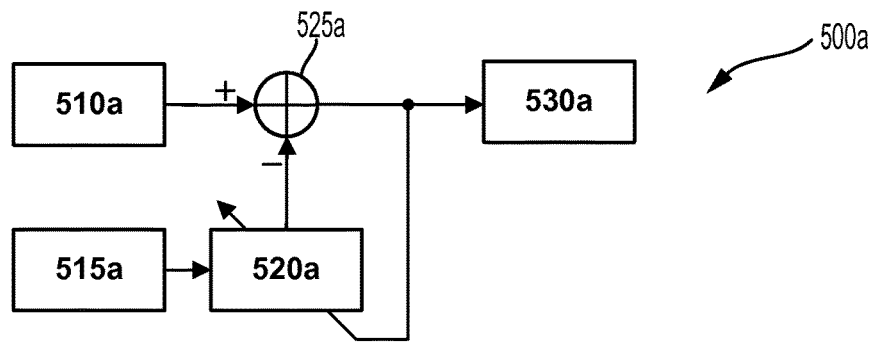
FIG. 5A is a diagram of an example system configured to remove a noise signal from a detected signal and to determine a pulse rate.

In a particular example, the artifact signal could be filtered and the filtered artifact signal could be subtracted from samples of the detected signal to generate samples of a filtered signal. As an illustrative example, FIG. 5A illustrates a system 500a that could be operated to determine a cardiovascular pulse rate. The system 500a includes a sensor 510a configured to obtain a plurality of samples of an input signal (e.g., to optically detect a blood volume signal, as described elsewhere herein) that is related to a cardiovascular pulse. The system 500a additionally includes an artifact sensor 515a (e.g., an accelerometer, a gyroscope, an ambient light sensor, a pressure transducer) configured to obtain a plurality of samples of an artifact signal that is related to unwanted content in the input signal (e.g., motion artifacts in the input signal that are related to relative motion between the sensor 510a and a target, e.g., a portion of subsurface vasculature). The samples of the artifact signal are filtered by an artifact filter 520a to generate a filtered artifact signal. The filtered artifact signal is subtracted 525a from the input signal to generate a plurality of filtered samples of the input signal. A cardiovascular pulse rate (or other rate or frequency of contents of the input signal) is detected by a rate detector 530a. The rate detector could be configured to determine one or more frequency spectra, to determine frequencies of peaks or local maxima thereof, to operate a plurality of digital PLLs, or to perform some other processes on one or more sets of samples of the generated samples of the filtered signal to determine one or more respective cardiovascular pulse rates (or other rate or frequency information).

The artifact filter 520a could be configured in a variety of ways to filter obtained samples of the artifact signal. For example, the artifact filter 520a could be configured as a finite impulse response (FIR) or infinite impulse response (IIR) filter. Coefficients or other properties of the artifact filter 520a could be selected such that the artifact filter 520a acts as a bandpass filter, a lowpass filter, or some other type of filter according to an application. For example, coefficients or other properties of the artifact filter 520a could be selected based on expected, detected, and/or otherwise determined statistical and/or spectral properties of the artifact signal and/or of the relationship between the artifact signal and the input signal (e.g., frequency- and/or time-dependent property of coupling of the artifact signal to unwanted contents of the input signal).

As shown in FIG. 5A, the samples of the filtered input signal could be used to update or modify the artifact filter 520a, e.g., to update coefficients or other properties of the artifact filter 520a in response, e.g., to changes in the relationship between the artifact signal and related content of the input signal. Such an update could be performed continuously (e.g., for each generated sample of the filtered input signal, at some other regular rate). Additionally or alternatively, such an update could be performed during initialization of the system 500a (e.g., when the sensor 510a is mounted to a skin surface), when a detected error and/or noise level or other detected property of the filtered input signal exceeds a threshold, or according to some other consideration.

In some examples, the artifact filter 520a could be a least mean squares (LMS) filter or a normalized least mean squares (NLMS) filter. That is, samples of the generated filtered input signal could be applied as an output error to the artifact filter 520a such that coefficients of the artifact filter 520a are updated to better predict contents of the input signal that are related to the artifact signal (e.g., to better predict motion artifacts in the input signal that are able to be predicted based on the artifact signal).

In examples wherein a frequency spectrum is determined and/or updated for each sample of an input signal (e.g., wherein a first frequency spectrum for a first set of samples of an input signal are determined by updating a second frequency spectrum for a second, overlapping, prior set of samples that is offset from the first set of samples by a single sample using a sliding DFT), frequency components of such a determined frequency spectrum could be filtered or otherwise modified based on obtained samples of an artifact signal. For example, a frequency spectrum of an artifact signal could be determined an each frequency component of the frequency spectrum of the input signal could be filtered based on a corresponding frequency component of the frequency spectrum of the artifact signal.

Figure 5B:
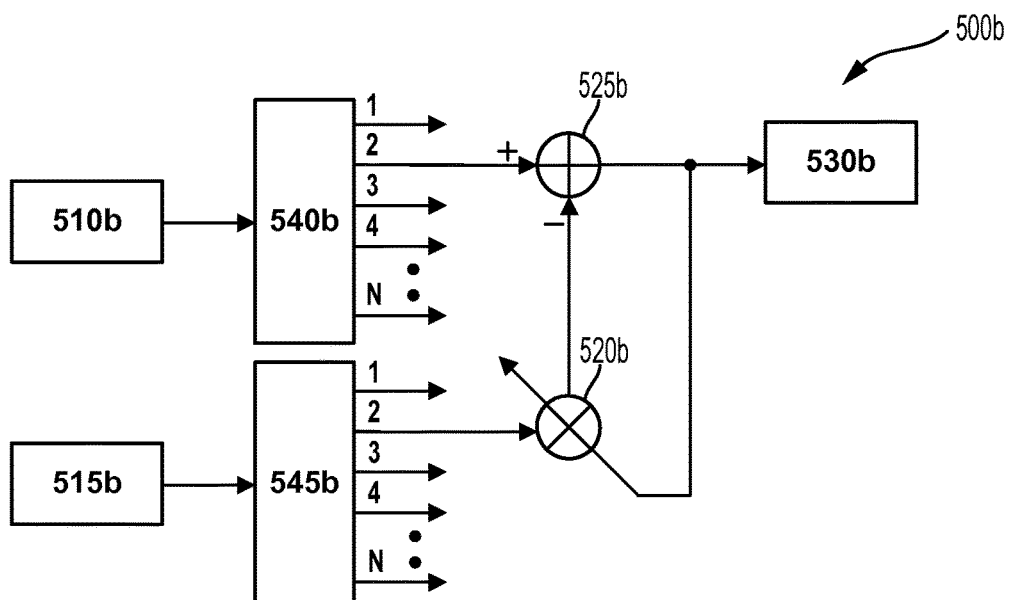
FIG. 5B is a diagram of an example system configured to remove a noise signal from a detected signal and to determine a pulse rate.

As an illustrative example, FIG. 5B illustrates a system 500b that could be operated to determine a cardiovascular pulse rate. The system 500b includes a sensor 510b configured to obtain a plurality of samples of an input signal (e.g., to optically detect a blood volume signal, as described elsewhere herein) that is related to a cardiovascular pulse. The system 500b additionally includes an artifact sensor 515b (e.g., an accelerometer, a gyroscope, an ambient light sensor, a pressure transducer) configured to obtain a plurality of samples of an artifact signal that is related to unwanted content in the input signal (e.g., motion artifacts in the input signal that are related to relative motion between the sensor 510b and a target, e.g., a portion of subsurface vasculature). Input and artifact frequency spectra are determined based on samples of the input signal and the artifact signal, respectively (represented by the discrete Fourier transformation blocks 540b, 545b, respectively). The input and artifact frequency spectra include respectively pluralities of corresponding frequency components (illustrated by the numbered taps).

A particular frequency component (the component illustrated as '2' in FIG. 5B) of the input frequency spectrum is filtered by a corresponding frequency component of the artifact frequency spectrum. As shown in FIG. 5B, this includes multiplying the frequency component of the artifact frequency spectrum by a factor 520b to generate a filtered artifact frequency component and subtracting 525b the filtered artifact frequency component from the input frequency component to generate a filtered frequency component. Such filtering could be performed for all of the frequency components of a determined frequency spectrum (not shown) or for a subset of the determined frequency components. A filtered input frequency spectrum (comprised of a plurality of such filtered or unfiltered input frequency components) can then be used to determine a cardiovascular pulse rate (or other rate or frequency of contents of the input signal) by a rate detector 530b. The rate detector could be configured to determine one or more frequency spectra, to determine frequencies of peaks or local maxima thereof, to operate a plurality of digital PLLs, or to perform some other processes on one or more determined filtered frequency spectra to determine one or more respective cardiovascular pulse rates (or other rate or frequency information).

As shown in FIG. 5B, the filtered input frequency components could be used to update or modify the multiplication factor 520b, e.g., to update the value of the multiplication factor 520b in response, e.g., to changes in the relationship between the artifact frequency component and related content of the input frequency component. Such an update could be performed continuously (e.g., for each generated input frequency component, at some other regular rate). Additionally or alternatively, such an update could be performed during initialization of the system 500b (e.g., when the sensor 510b is mounted to a skin surface), when a detected error and/or noise level or other detected property of the filtered input frequency component(s) exceeds a threshold, or according to some other consideration. In some examples, the multiplication factor 520b could be updated according to a least mean squares (LMS) filter or a normalized least mean squares (NLMS) filter. That is, generated filtered input frequency components could be applied as an output error to the multiplication factor 520b such that the value of the multiplication factor 520b is updated to better predict contents of the input frequency component that are related to the artifact frequency component (e.g., to better predict motion artifacts in the input signal at the frequency corresponding to the particular frequency component that are able to be predicted based on the artifact signal at that frequency).

Figure 5C:
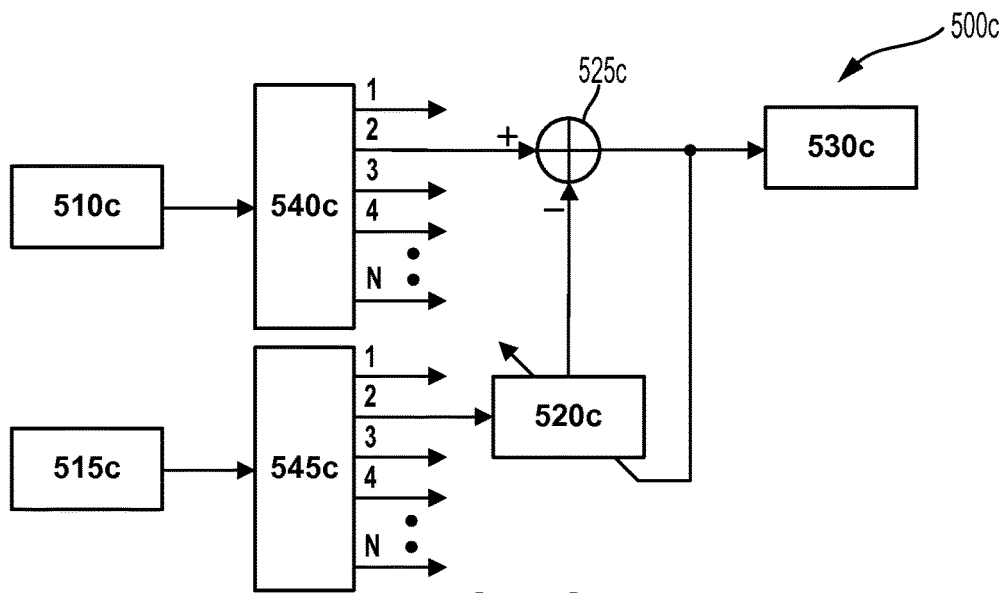
FIG. 5C is a diagram of an example system configured to remove a noise signal from a detected signal and to determine a pulse rate.

Further, such filtering of generated frequency components could include filtering frequency components of an artifact frequency spectrum using a filter having an order greater than one (e.g., an FIR, an IIR). As an illustrative example, FIG. 5C illustrates a system 500c that could be operated to determine a cardiovascular pulse rate. The system 500c includes a sensor 510c configured to obtain a plurality of samples of an input signal (e.g., to optically detect a blood volume signal, as described elsewhere herein) that is related to a cardiovascular pulse. The system 500c additionally includes an artifact sensor 515c (e.g., an accelerometer, a gyroscope, an ambient light sensor, a pressure transducer) configured to obtain a plurality of samples of an artifact signal that is related to unwanted content in the input signal (e.g., motion artifacts in the input signal that are related to relative motion between the sensor 510b and a target, e.g., a portion of subsurface vasculature). Input and artifact frequency spectra are determined based on samples of the input signal and the artifact signal, respectively (represented by the discrete Fourier transformation blocks 540c, 545c, respectively). The input and artifact frequency spectra include respectively pluralities of corresponding frequency components (illustrated by the numbered taps). A particular frequency component (the component illustrated as '2' in FIG. 5C) of the input frequency spectrum is filtered by a corresponding frequency component of the artifact frequency spectrum to generate a filtered input frequency component. As shown in FIG. 5C, this includes using an artifact filter 520c to generate a filtered artifact frequency component. The filtered artifact frequency component is subtracted 525c from the corresponding input frequency component to generate the filtered input frequency component.

Such filtering could be performed for all of the frequency components of a determined frequency spectrum (not shown) or for a subset of the determined frequency components. A filtered input frequency spectrum (comprised of a plurality of such filtered or unfiltered input frequency components) can then be used to determine a cardiovascular pulse rate (or other rate or frequency of contents of the input signal) by a rate detector 530c. The rate detector could be configured to determine one or more frequency spectra, to determine frequencies of peaks or local maxima thereof, to operate a plurality of digital PLLs, or to perform some other processes on one or more determined filtered frequency spectra to determine one or more respective cardiovascular pulse rates (or other rate or frequency information).

The artifact filter 520c could be configured in a variety of ways to filter determined artifact frequency components. For example, the artifact filter 520c could be configured as a finite impulse response (FIR) or infinite impulse response (IIR) filter. Coefficients or other properties of the artifact filter 520c could be selected such that the artifact filter 520c acts as a bandpass filter, a lowpass filter, or some other type of filter according to an application. For example, coefficients or other properties of the artifact filter 520c could be selected based on expected, detected, and/or otherwise determined statistical and/or spectral properties of the artifact signal (e.g., of particular frequency components of the artifact signal) and/or of the relationship between the artifact signal and the input signal (e.g., frequency- and/or time-dependent property of coupling of the artifact signal to unwanted contents of the input signal).

As shown in FIG. 5C, generated filtered input frequency components could be used to update or modify the artifact filter 520c, e.g., to update coefficients or other properties of the artifact filter 520c in response, e.g., to changes in the relationship between the artifact signal and related content of the input signal. Such an update could be performed continuously (e.g., for each generated sample of the filtered input signal, at some other regular rate). Additionally or alternatively, such an update could be performed during initialization of the system 500c (e.g., when the sensor 510c is mounted to a skin surface), when a detected error and/or noise level or other detected property of the filtered input signal exceeds a threshold, or according to some other consideration.

In some examples, the artifact filter 520c could be a least mean squares (LMS) filter or a normalized least mean squares (NLMS) filter. That is, determined filtered input frequency components could be applied as an output error to the artifact filter 520c such that coefficients of the artifact filter 520c are updated to better predict contents of generated input frequency components that are related to the artifact signal (e.g., to better predict motion artifacts in the input signal that are able to be predicted based on the artifact signal).

Note that the use of LMS and/or NLMS filters is intended as a non-limiting example of an adaptive filter that could be used to filter an artifact signal in order to remove unwanted content from an input signal. Further, a multiple-valued artifact signal (e.g., an artifact signal generated by an accelerometer that includes values related to acceleration in three different directions) could be used to filter an input signal. In some examples, this could include determining a single-valued function from the multiple values of the artifact signal (e.g., determining a magnitude of overall acceleration based on detected accelerations in three different directions). Additionally or alternatively, each of the values or signals of the artifact signal could be used to filter the input signal. For example, a first filtered input signal could be determined by filtering an input signal based on a first artifact signal. The first filtered input signal could then be filtered based on a second artifact signal to generate a second filtered input signal. Other methods of removing unwanted content (e.g., noise, motion artifact, amplitude variations) from a detected signal based on an artifact signal related to the unwanted content are anticipated.

V. EXAMPLE DEVICES

Figure 6:
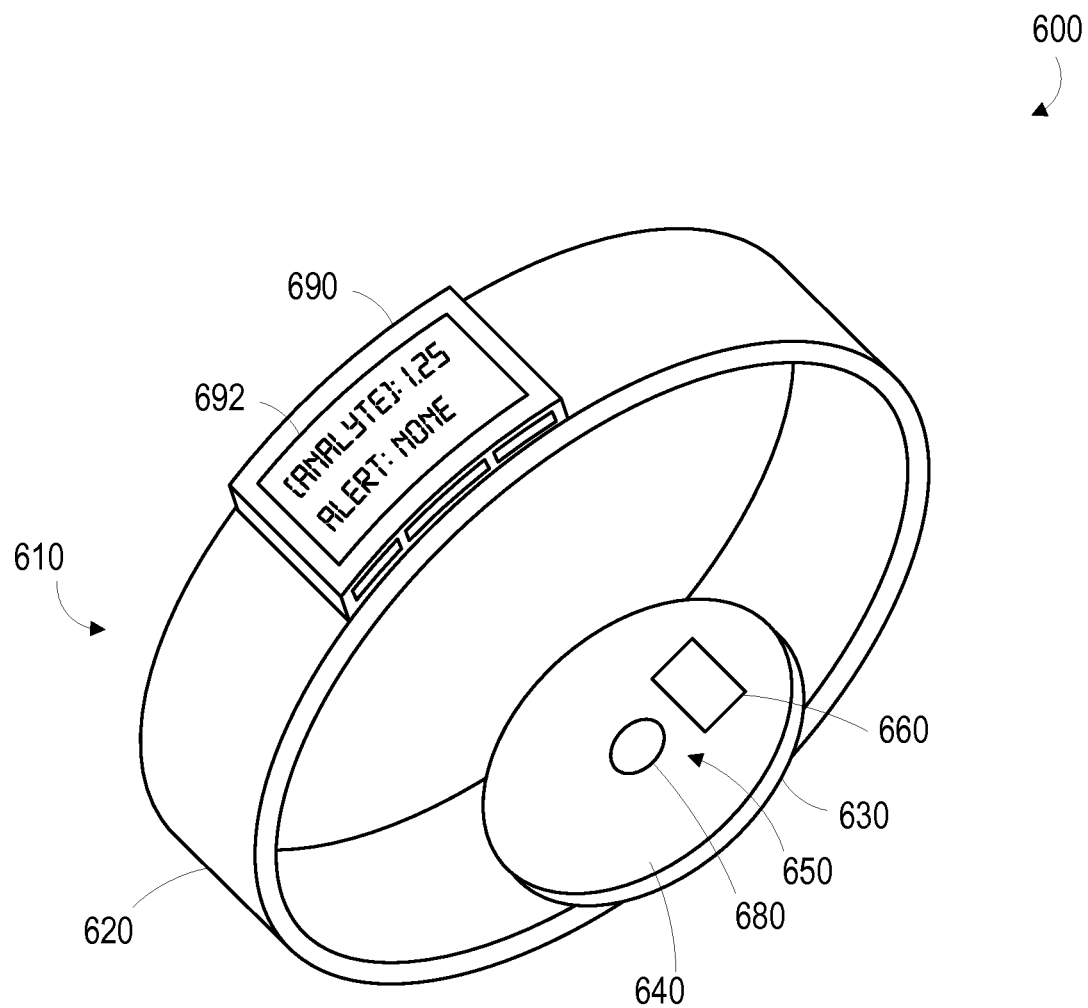
FIG. 6 is a perspective view of an example wearable device.

A wearable device 600 (illustrated in FIG. 6) can automatically measure a cardiovascular pulse rate of blood in a portion of subsurface vasculature (or of some other tissue or cells) of a person wearing the device. The term "wearable device," as used in this disclosure, refers to any device that is capable of being worn at, on or in proximity to a body surface, such as a wrist, ankle, waist, chest, or other body part. In order to take in vivo measurements in a non-invasive manner from outside of the body, the wearable device may be positioned on a portion of the body where subsurface vasculature or some other tissue containing pulsatile blood flow is easily observable, the qualification of which will depend on the type of detection system used. The device may be placed in close proximity to the skin or tissue, but need not be touching or in intimate contact therewith. A mount 610, such as a belt, wristband, ankle band, etc. can be provided to mount the device at, on or in proximity to the body surface. The mount 610 may prevent the wearable device from moving relative to the body to reduce measurement error and noise. In one example, shown in FIG. 6, the mount 610, may take the form of a strap or band 620 that can be worn around a part of the body. Further, the mount 610 may be an adhesive substrate for adhering the wearable device 600 to the body of a wearer.

A measurement platform 630 is disposed on the mount 610 such that it can be positioned on the body where subsurface vasculature is easily observable. An inner face 640 of the measurement platform is intended to be mounted facing to the body surface. The measurement platform 630 may house a data collection system 650, which may include at least a light source 680 (e.g., an LED, a laser) configured to emit illumination into a portion of subsurface vasculature. The measurement platform 630 additionally includes a light sensor 660 configured to detect the intensity of other properties of light emitted from (e.g., reflected from, refracted by, scattered by) the portion of subsurface vasculature in response the illumination emitted from the light source 680. In a non-exhaustive list, the light sensor 660 may include one or more of a photodiode, a phototransistor, a photoresistor, an active pixel sensor, a CCD, a camera, a spectrometer, an interferometer, or some other light sensitive element configured to detect one or more properties of the emitted light. The components of the data collection system 650 may be miniaturized so that the wearable device may be worn on the body without significantly interfering with the wearer's usual activities.

The data collection system 650 may additionally include additional detectors for detecting other physiological parameters, which could include any parameters that may relate to the health of the person wearing the wearable device. For example, the data collection system 650 could include detectors configured to measure blood pressure, respiration rate, skin temperature, etc. In a non-exhaustive list, additional detectors may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor.

The light source 680 is configured to transmit illumination that can penetrate the wearer's skin into the portion of subsurface vasculature, for example, into a lumen of the subsurface vasculature. The transmitted illumination can be any kind of illumination that is benign to the wearer and that results at least in an amount of absorption by blood in the subsurface vasculature that is related to the volume of the blood in the subsurface vasculature, e.g., such that light responsively emitted from the body has one or more detectable properties related to the volume of flow and/or the pulse rate of blood in the portion of subsurface vasculature (e.g., an intensity related to the amount of blood in the portion of subsurface vasculature). The wavelength of the transmitted illumination could be specified to penetrate biological tissues of a wearer; for example, the transmitted illumination could have a wavelength within a near-infrared (NIR) transparency window of biological tissue (e.g., between approximately 650 nanometers and approximately 950 nanometers and/or between approximately 1000 nanometers and approximately 1350 nanometers). The wavelength of the transmitted illumination could be specified to be a wavelength that is absorbed and/or scattered by blood cells. The wavelength of the transmitted illumination could be between approximately 400 nanometers and approximately 1000 nanometers.

The wearable device 600 may also include a user interface 690 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 690 may include a display 692 where a visual indication of the alert or recommendation may be displayed. The display 692 may further be configured to provide an indication of the measured physiological parameters, for instance, a determined cardiovascular pulse rate.

Figure 7A:
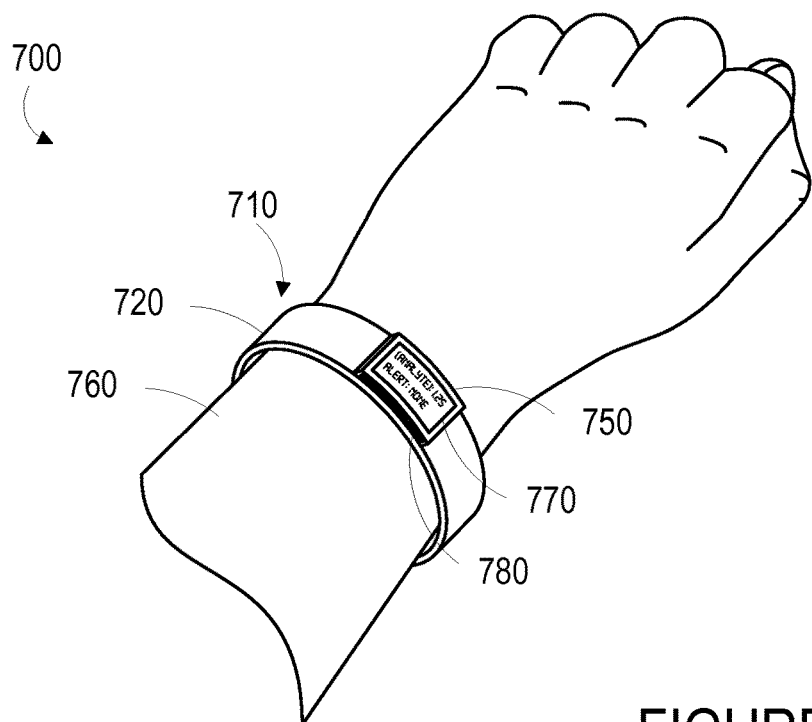
FIG. 7A is a perspective top view of an example wrist-mounted device, when mounted on a wearer's wrist.
Figure 7B:
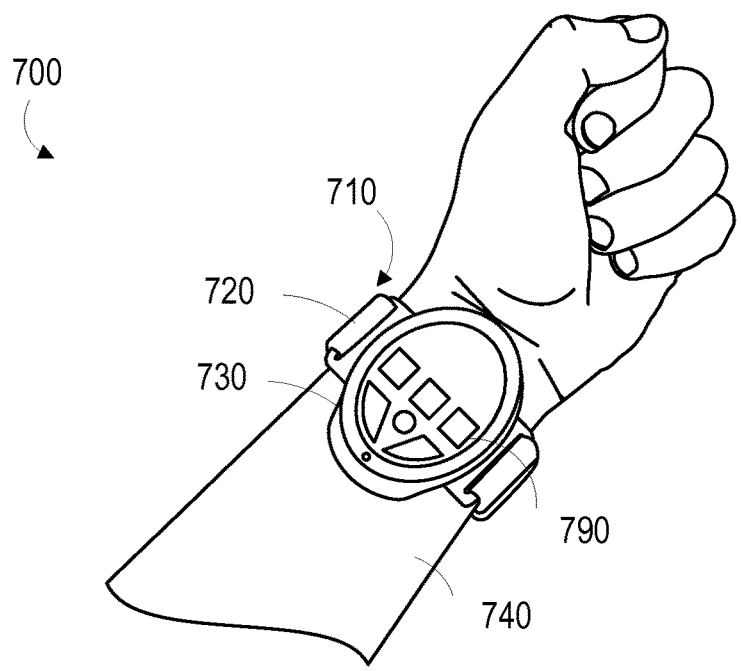
FIG. 7B is a perspective bottom view of an example wrist-mounted device shown in FIG. 7A, when mounted on a wearer's wrist.

In some examples, the wearable device is provided as a wrist-mounted device, as shown in FIGS. 7A and 7B. The wrist-mounted device may be mounted to the wrist of a living subject with a wristband or cuff, similar to a watch or bracelet. As shown in FIGS. 7A and 7B, the wrist mounted device 700 may include a mount 710 in the form of a wristband 720, a measurement platform 730 positioned on the anterior side 740 of the wearer's wrist, and a user interface 750 positioned on the posterior side 760 of the wearer's wrist. The wearer of the device may receive, via the user interface 750, one or more recommendations or alerts generated either from a remote server or other remote computing device, or alerts from the measurement platform. Such a configuration may be perceived as natural for the wearer of the device in that it is common for the posterior side 760 of the wrist to be observed, such as the act of checking a wrist-watch. Accordingly, the wearer may easily view a display 770 on the user interface. Further, the measurement platform 730 may be located on the anterior side 740 of the wearer's wrist where the subsurface vasculature may be readily observable. However, other configurations are contemplated.

The display 770 may be configured to display a visual indication of the alert or recommendation and/or an indication of the measured physiological parameters, for instance, a cardiovascular pulse rate or other physiological property detected by the device 700. Further, the user interface 750 may include one or more buttons 780 for accepting inputs from the wearer. For example, the buttons 780 may be configured to change the text or other information visible on the display 770. As shown in FIG. 7B, measurement platform 730 may also include one or more buttons 790 for accepting inputs from the wearer. The buttons 790 may be configured to accept inputs for controlling aspects of the data collection system, such as initiating a measurement period, or inputs indicating the wearer's current health state (i.e., normal, migraine, shortness of breath, heart attack, fever, "flu-like" symptoms, food poisoning, etc.).

Figure 8:
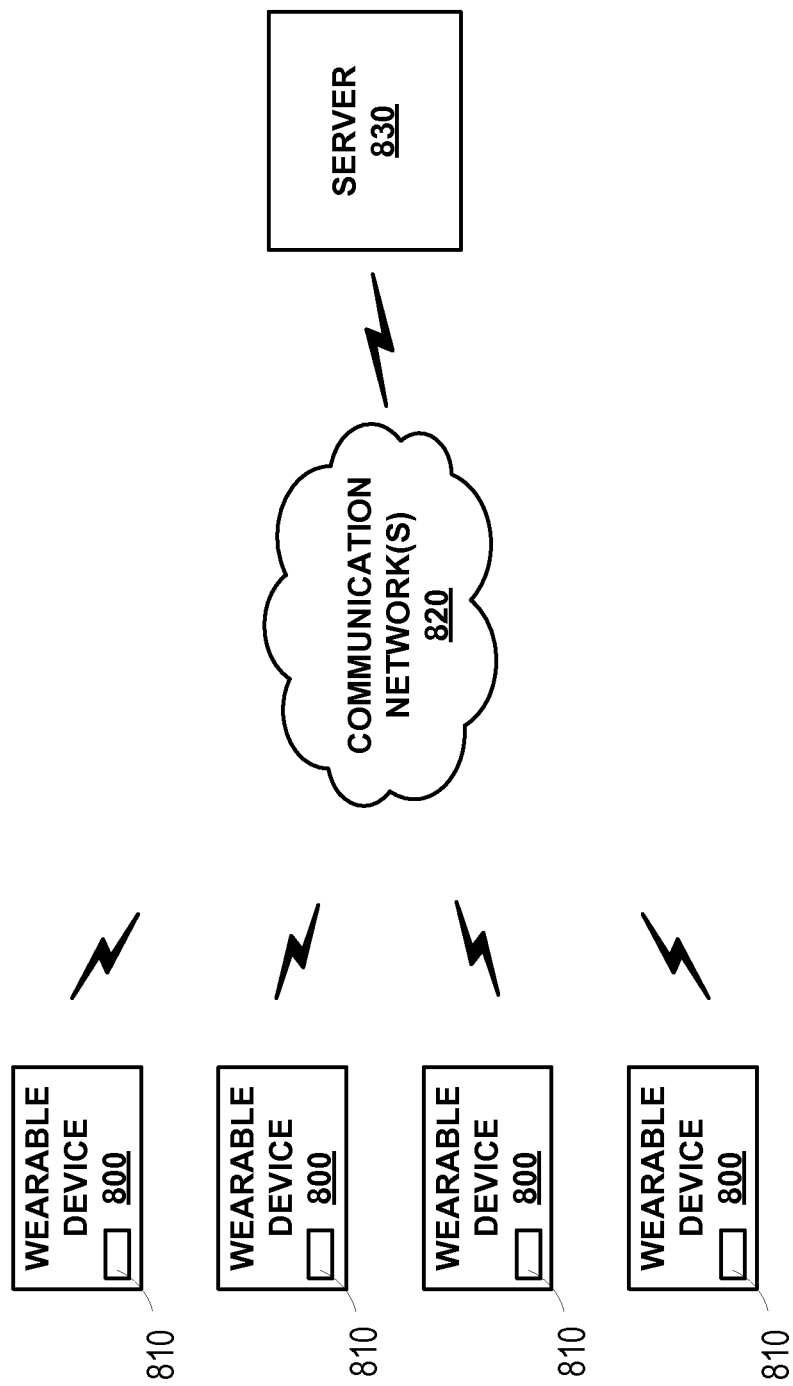
FIG. 8 is a block diagram of an example system that includes a plurality of wearable devices in communication with a server.

FIG. 8 is a simplified schematic of a system including one or more wearable devices 800. The one or more wearable devices 800 may be configured to transmit data via a communication interface 810 over one or more communication networks 820 to a remote server 830. In one embodiment, the communication interface 810 includes a wireless transceiver for sending and receiving communications to and from the server 830. In further embodiments, the communication interface 810 may include any means for the transfer of data, including both wired and wireless communications. For example, the communication interface may include a universal serial bus (USB) interface or a secure digital (SD) card interface. Communication networks 820 may be any one of may be one of: a plain old telephone service (POTS) network, a cellular network, a fiber network and a data network. The server 830 may include any type of remote computing device or remote cloud computing network. Further, communication network 820 may include one or more intermediaries, including, for example wherein the wearable device 800 transmits data to a mobile phone or other personal computing device, which in turn transmits the data to the server 830.

In addition to receiving communications from the wearable device 800, such as collected physiological parameter data and data regarding health state as input by the user, the server may also be configured to gather and/or receive either from the wearable device 800 or from some other source, information regarding a wearer's overall medical history, environmental factors and geographical data. For example, a user account may be established on the server for every wearer that contains the wearer's medical history. Moreover, in some examples, the server 830 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

The server may also be configured to make determinations regarding the efficacy of a drug or other treatment based on information regarding the drugs or other treatments received by a wearer of the device and, at least in part, the physiological parameter data and the indicated health state of the user. From this information, the server may be configured to derive an indication of the effectiveness of the drug or treatment. For example, if a drug is intended to treat nausea and the wearer of the device does not indicate that he or she is experiencing nausea after beginning a course of treatment with the drug, the server may be configured to derive an indication that the drug is effective for that wearer. In another example, if a wearer is prescribed a drug intended to treat tachycardia, but the server receives data from the wearable device indicating (based on a determined pulse rate and/or a plurality of detected samples of a photoplethysmographic signal) that the wearer's heart rate has remained elevated over a certain number of measurement periods, the server may be configured to derive an indication that the drug is not effective for its intended purpose for this wearer.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

VI. EXAMPLE ELECTRONICS PLATFORM FOR A DEVICE

Figure 9:
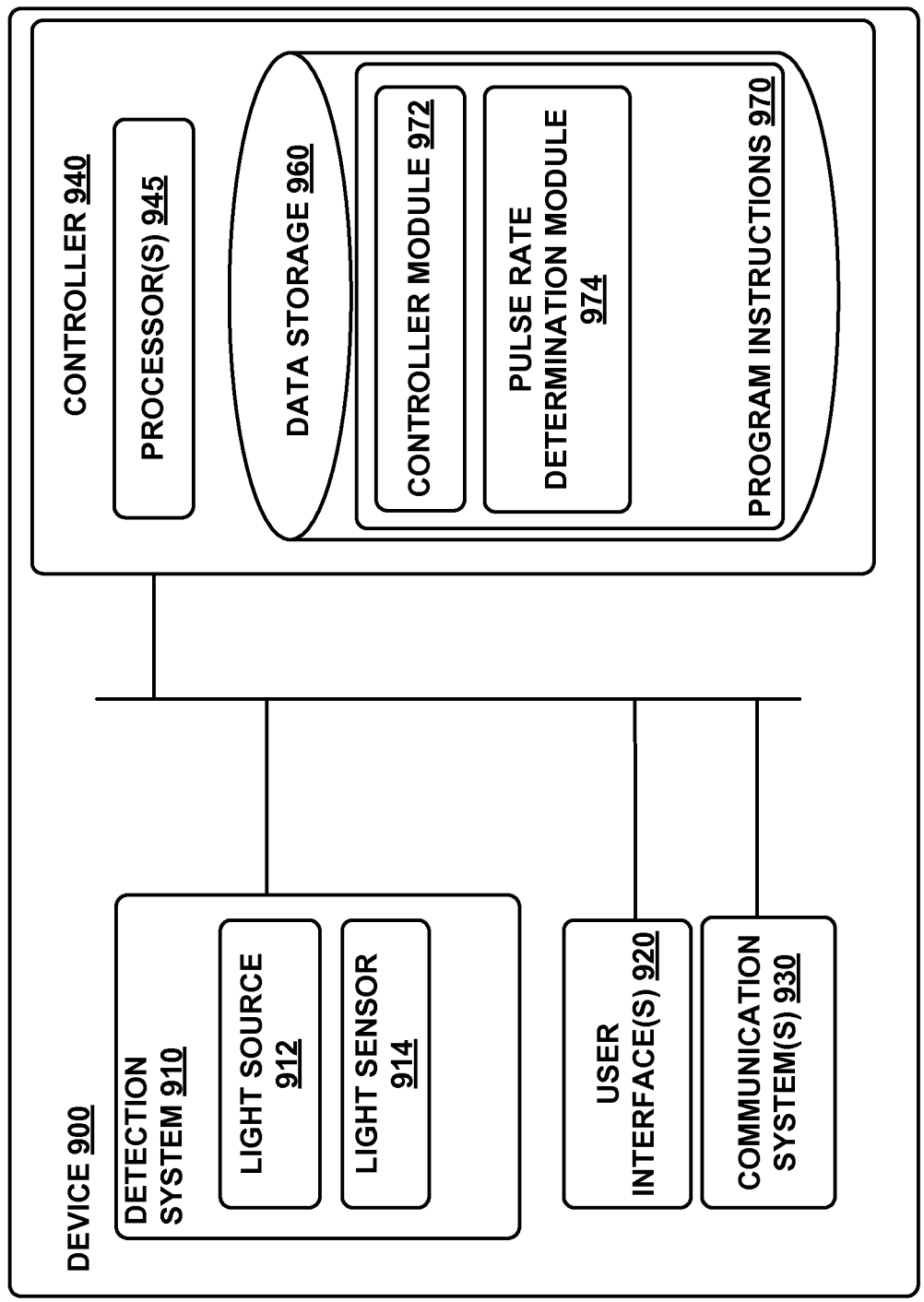
FIG. 9 is a functional block diagram of an example device.

FIG. 9 is a simplified block diagram illustrating the components of a device 900, according to an example embodiment. Device 900 may take the form of or be similar to the devices 600, 700 shown in FIGS. 6 and 7. That is, device 900 may take the form of a wrist-mountable or otherwise body-mountable device. Device 900 may also take other forms, e.g., could take the form of a device configured to be maintained in proximity to an environment of interest (e.g., a body part) by a user or operator of the device 900 or by a frame or other supporting structure. Device 900 could also take the form of a device configured to illuminate and to detect emitted light from some other environment, for example, a body of an animal or some other environment containing a parameter or variable that could be detected optically and that contains an oscillating pattern having a frequency or rate that could be detected according to the methods described herein. Device 900 also could take other forms.

In particular, FIG. 9 shows an example of a device 900 having a detection system 910, a user interface 920, communication system(s) 930 for transmitting data to a remote system, and controller 940. The components of the device 900 may be disposed on a mount or on some other structure for mounting the device to enable stable detection of a photoplethysmographic signal from a portion of subsurface vasculature, for example, around a wrist of a wearer such that a portion of subsurface vasculature is visible.

Controller 940 may be provided as a computing device that includes one or more processors 945. The one or more processors 945 can be configured to execute computer-readable program instructions 970 that are stored in the computer readable data storage 960 and that are executable to provide the functionality of a device 900 described herein.

The computer readable data storage 960 may include or take the form of one or more non-transitory, computer-readable storage media that can be read or accessed by at least one processor 945. The one or more computer-readable storage media can include volatile and/or non-volatile storage components, such as optical, magnetic, organic or other memory or disc storage, which can be integrated in whole or in part with at least one of the one or more processors 945. In some embodiments, the computer readable data storage 960 can be implemented using a single physical device (e.g., one optical, magnetic, organic or other memory or disc storage unit), while in other embodiments, the computer readable data storage 960 can be implemented using two or more physical devices.

Detection system 910 includes a light sensor 914 and a light source 912. The light source 912 is configured to emit illumination into an environment of interest (e.g., into a portion of subsurface vasculature). The detection system 910 additionally includes a light sensor 914 configured to detect one or more properties of light emitted from the portion of subsurface vasculature in response to illumination emitted from the light source 912. In a non-exhaustive list, the light sensor 914 may include one or more of a photodiode, a phototransistor, a photoresistor, an active pixel sensor, a CCD, a camera, a spectrometer, an interferometer, or some other light sensitive element configured to detect one or more properties of the emitted light.

The detection system 910 may additionally include additional detectors for detecting additional or alternative properties of the environment of interest (e.g., for detecting physiological parameters of a human whose body includes the environment of interest). Such additional detected properties could include any parameters that may relate to the health of the person whose biological tissues are being measured by the device 900. For example, the detection system 910 could include detectors configured to measure blood pressure, respiration rate, skin temperature, etc. In a non-exhaustive list, additional detectors may include any one of an optical (e.g., CMOS, CCD, photodiode), acoustic (e.g., piezoelectric, piezoceramic), electrochemical (voltage, impedance), thermal, mechanical (e.g., pressure, strain, acceleration, angular acceleration), magnetic, or electromagnetic (e.g., magnetic resonance) sensor. Further, a frequency or rate of oscillating patterns within such detected parameters could be determined according to the methods described herein. Additionally or alternatively, such signals could be operated to detect an artifact signal that could be used to filter noise from one or more signals of interest.

The detection system 910 could additionally include electronics configured to operate the light source 912 and the light sensor 914. The electronics could include a high-speed analog-to-digital converter (ADC) configured to sample an output (e.g., a voltage, a current) of one or more light-sensitive elements of the light sensor 914. Additionally or alternatively, the electronics could include analog frontend circuitry that includes analog circuitry configured to filter, decimate, quantize, or otherwise alter and/or perform other analog operations or computations on the output(s) of the light source 914 to produce an output electronic signal that is related to physiological properties or other parameters in the environment. This output electronic signal(s) could then be used (e.g., sampled by an ADC of a microcontroller) to determine the cardiovascular pulse rate of a wearer.

The program instructions 970 stored on the computer readable data storage 960 may include instructions to perform any of the methods described herein. For instance, in the illustrated embodiment, program instructions 970 include a controller module 972 and a pulse rate determination module 974.

The controller module 972 can include instructions for operating the detection system 910, for example, the light source 912 and the light sensor 914. For example, the controller module 972 may operate the light source 912 and the light sensor 914 at a plurality of points in time to obtain a respective plurality of samples of a photoplethysmographic signal. In particular, the controller module 972 can include instructions for operating the light source 912 to emit illumination into a target environment (e.g., tissue of a person) and controlling the light sensor 914 to detect an intensity or other properties of light emitted from the environment responsive to the illumination.

The controller module 972 can also include instructions for operating a user interface 920. For example, controller module 972 may include instructions for displaying data collected by the detection system 910 and analyzed by the pulse rate determination module 974. Further, controller module 972 may include instructions to execute certain functions based on inputs accepted by the user interface 920, such as inputs accepted by one or more buttons or touchscreen displays disposed on the user interface.

Pulse rate determination module 974 may include instructions for receiving data from and/or operating the data collection system 910, analyzing the data to determine cardiovascular pulse rates, to determine based on such determined pulse rates or other information if a medical condition is indicated (e.g., an arrhythmia, a heart attack, a cardiac arrest), or other analytical processes relating to the environment proximate to the device 900. In particular, the pulse rate determination module 974 may include instructions for determining frequency spectra, operating digital phase locked loops, removing noise from one or more signals of interest based on an artifact signal detected by the device 900 (e.g., by an accelerometer of the device), or for performing some other operations or methods as described herein.

Some of the program instructions of the controller module 972 and the pulse rate determination module 974 may, in some examples, be stored in a computer-readable medium and executed by a processor located external to the device 900. For example, the device 900 could be configured to illuminate and to receive light from portion of biological tissue (or to otherwise generate or obtain a plurality of samples of a signal of interest) and then transmit related data to a remote server, which may include a mobile device, a personal computer, the cloud, or any other remote system, for further processing (e.g., for the determination of pulse rates and/or frequencies of oscillating patterns in the received light using methods described herein).

User interface 920 could include indicators, displays, buttons, touchscreens, head-mounted displays, and/or other elements configured to present information about the device 900 to a user and/or to allow the user to operate the device 900. Additionally or alternatively, the device 900 could be configured to communicate with another system (e.g., a cellphone, a tablet, a computer, a remote server) and to present elements of a user interface using the remote system. The user interface 920 could be disposed proximate to the light source 912, light sensor 914, or other elements of the device 900 or could be disposed away from other elements of the device 900 and could further be in wired or wireless communication with the other elements of the device 900. The user interface 920 could be configured to allow a user to specify some operation, function, or property of operation of the device 900. The user interface 920 could be configured to present a determined pulse rate of blood in a portion of subsurface vasculature or some other health state of a wearer of the device 900, or to present some other information to a user. Other configurations and methods of operation of a user interface 920 are anticipated.

Communication system(s) 930 may also be operated by instructions within the program instructions 970, such as instructions for sending and/or receiving information via a wireless antenna, which may be disposed on or in the device 900. The communication system(s) 930 can optionally include one or more oscillators, mixers, frequency injectors, etc. to modulate and/or demodulate information on a carrier frequency to be transmitted and/or received by the antenna. In some examples, the device 900 is configured to indicate an output from the controller 940 by transmitting an electromagnetic or other wireless signal according to one or more wireless communications standards (e.g., Bluetooth, WiFi, IRdA, ZigBee, WiMAX, LTE). In some examples, the communication system(s) 930 could include one or more wired communications interfaces and the device 900 could be configured to indicate an output from the controller 940 by operating the one or more wired communications interfaces according to one or more wired communications standards (e.g., USB, FireWire, Ethernet, RS-232).

The computer readable data storage 960 may further contain other data or information, such as scattering, absorption, or other optical properties of tissues of a user of the device 900, that may be useful in determining pulse rates or other physiological parameters. Further, the computer readable data storage 960 may contain data corresponding to pulse rate transition probabilities or other property baselines that describe expected changes in cardiovascular pulse rate or other properties of biological tissues and/or of a body. The baselines may be pre-stored on the computer readable data storage 960, may be transmitted from a remote source, such as a remote server, or may be generated by the pulse rate determination module 974 itself. The pulse rate determination module 974 may include instructions for generating individual baselines for the user of the device 900 based on data collected over a certain period of time. For example, the pulse rate determination module 974 may generate a baseline set of transition probabilities or other statistics describing expected changes in pulse rate over time based on cardiovascular pulse determined based on photoplethysmographic signals detected from portions of subsurface vasculature. The pulse rate determination module 974 could store those baselines in the computer readable data storage 960 for later use (e.g., to apply a forward-backward filter to a set of determined pulse rates or to perform some other filtering or determination related to a cardiovascular pulse). Baselines may also be generated by a remote server and transmitted to the device 900 via communication system(s) 930.

In some examples, obtained samples of a photoplethysmographic signal or other physiological property or parameter of interest, determined pulse rates, or other information generated by the device 900 may additionally be input to a cloud network and be made available for download by a user's physician. Analyses may also be performed on the collected data, such as estimates of pulse rate variability, arrhythmia, determinations of post-surgical treatment or rehabilitation regimens, and/or efficacy of drug treatment regimens, in the cloud computing network and be made available for download by physicians or clinicians. Further, collected information from individuals or populations of device users may be used by physicians or clinicians in monitoring efficacy of a surgical intervention or other treatment.

VII. ILLUSTRATIVE METHODS

Figure 10:
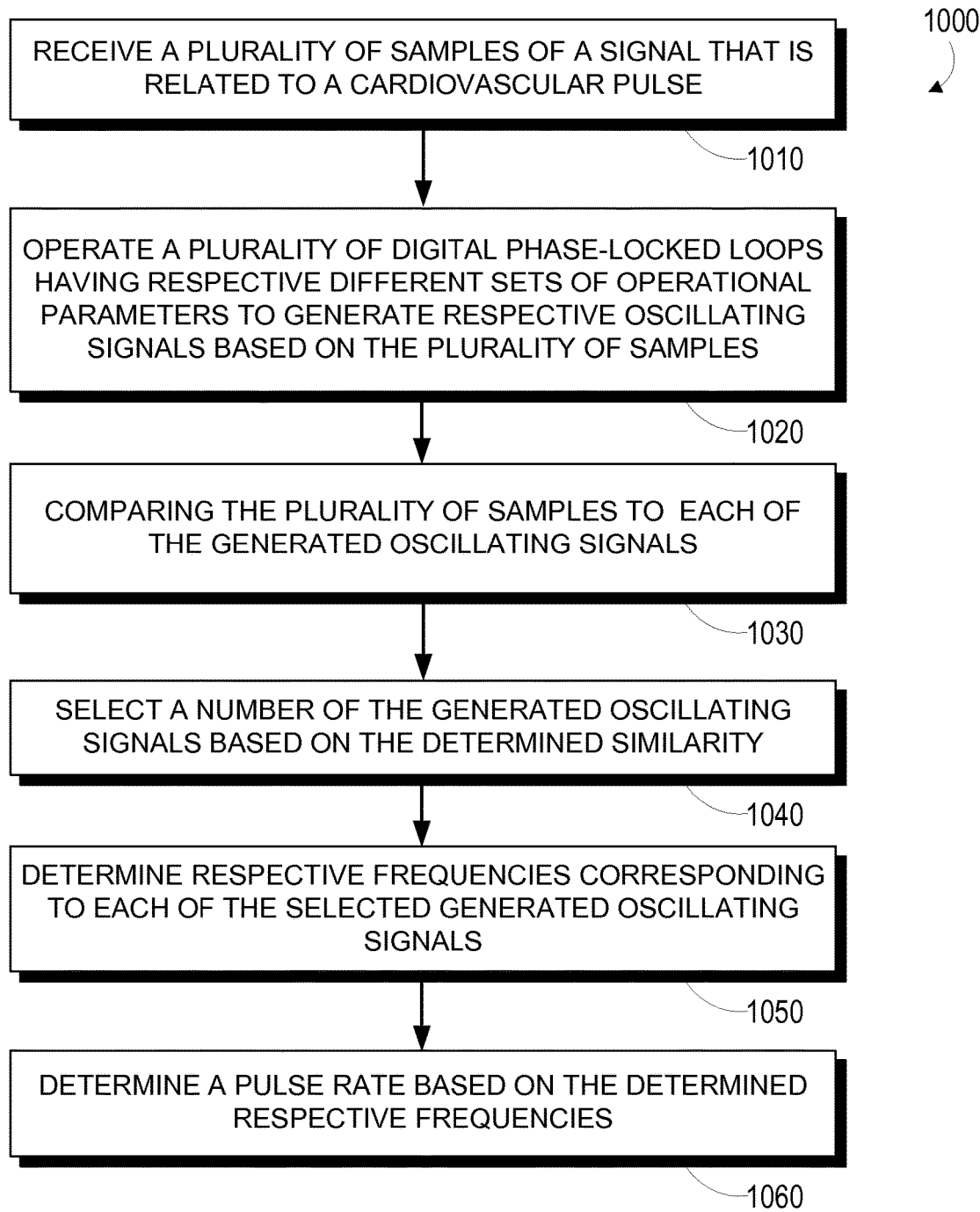
FIG. 10 is a flow chart of an example method.

FIG. 10 is a flowchart of a method 1000 for measuring a cardiovascular pulse rate. The method 1000 includes receiving a plurality of samples of a signal that is related to a cardiovascular pulse (1010). This could include operating a sensor to detect an intensity of light, a pattern of constructive and destructive interference in received light, a pressure, a temperature, an acceleration, a displacement, a color, a flow rate, or some other property related to a cardiovascular pulse, e.g., using a pressure sensor, a light sensor, a light emitter, a tonometer, an ultrasonic transducer, or some other sensing means. In some examples, receiving a plurality of samples of a signal that is related to a cardiovascular pulse (1010) could include receiving a plurality of samples of a plethysmographic signal, i.e., a signal related to a volume of blood in a portion of subsurface vasculature. Receiving such samples could include operating a light source to illuminate the portion of subsurface vasculature and operating a light sensor to detect an intensity or other property of light responsively emitted from the portion of subsurface vasculature.

The method 1000 additionally includes operating a plurality of digital phase locked loop (PLLs) having respective different sets of operational parameters to generate respective oscillating signals based on the plurality of samples (1020). This can include each of the digital PLLs having a different free-running frequency, initial state(s), adaptation rate, loop bandwidth, or some other properties that are different. Such different properties could be specified according to previously determined pulse rate, e.g., free-running frequencies, initial frequencies, or some other operational parameters of the digital PLLs could be specified based on a previously determined pulse rate.

The method 1000 additionally includes comparing the plurality of samples and each of the generated oscillating signals (1030). This can include determining a correlation (e.g., a Pearson product-moment correlation coefficient), a sum of squared differences, a sum of differences, a weighted sum of squared differences, a product of differences, a product of squared differences or some other determination, a function of such determinations (e.g., a nonlinear function of a sum of squared differences), and/or combination of determinations. The comparison between the plurality of samples and each of the generated oscillating signals (1030) could include performing a comparison based on all of the plurality of samples and corresponding samples of each of the oscillating signals generated by the plurality of digital. Alternatively, comparing the plurality of samples to each of the generated oscillating signals (1030) could include comparing a subset of the plurality of samples (e.g., the final 10% of the plurality of samples) to corresponding samples of each of the generated oscillating signals.

The method 1000 additionally includes selecting a number of the generated oscillating signals based on the comparison (1040). In some examples, this can include selecting a specified number of the oscillating signals, e.g., could include selecting the specified number of the oscillating signals that are the most similar to the plurality of samples. Alternatively, selecting a number of the generated oscillating signals (1040) could include selecting any oscillating signals corresponding to determined correlation coefficients or other measures of similarity that are greater than a specified value. Selecting a number of the generated oscillating signals (1040) could include selecting a specified or variable number of the generated oscillating signals according to some other method.

The method 1000 additionally includes determining respective frequencies corresponding to each of the selected generated oscillating signals (1050). This can include determining each frequency based on an internal state, e.g., a final frequency of a controlled-frequency oscillator, of a corresponding digital PLL of the operated plurality of digital PLLs. The frequencies could be determined in some other way (e.g., based on a peak-to-peak interval of the generated oscillating signals).

The method 1000 additionally includes determining a pulse rate based on the determined respective frequencies (1060). This can include combining determined frequencies of selected generated oscillating signals to generate a cardiovascular pulse rate in a variety of ways. In some examples, determining a pulse rate based on the determined respective frequencies (1060) could include determining an average (e.g., a linear average, a geometric average) of the determined frequencies. In some examples, determining a pulse rate based on the determined respective frequencies (1060) could include determining a weighted average or other combination of the determined frequencies, e.g., weighting the determined frequencies according to corresponding determined measures of similarity (e.g., such that a determined pulse rate is weighted toward frequencies corresponding to generated oscillating signals that are more similar to the plurality of samples of the detected signal). Determining a pulse rate based on the determined respective frequencies (1060) could include combining determined frequencies of selected generated oscillating signals to generate a pulse rate according to some other method.

The method 1000 could include additional steps or elements in addition to those illustrated in FIG. 10. For example, the method 1000 could include detecting an artifact signal and using the artifact signal to remove unwanted content (e.g., noise content, motion artifact content) of the obtained plurality of samples that is related to the artifact signal. The method 1000 could include indicating a determined pulse rate or other determined information to a user using a user interface. The method 1000 could be performed a plurality of times for a respectively plurality of sets of obtained samples of the signal. Further, a plurality of pulse rates determined from such operations could be filtered (e.g., using a bidirectional statistical filter) to provide improved estimates of the pulse rates. In some examples, a pulse rate determined using the method 1000 could be used to select a peak, local maximum, or other feature of a frequency spectrum determined from the plurality of samples and an improved (e.g., higher frequency resolution) estimate of the pulse rate could be determined based on the selected peak, local maximum, or other feature. Additional and/or alternative steps of the method 1100 are anticipated.

Figure 11:
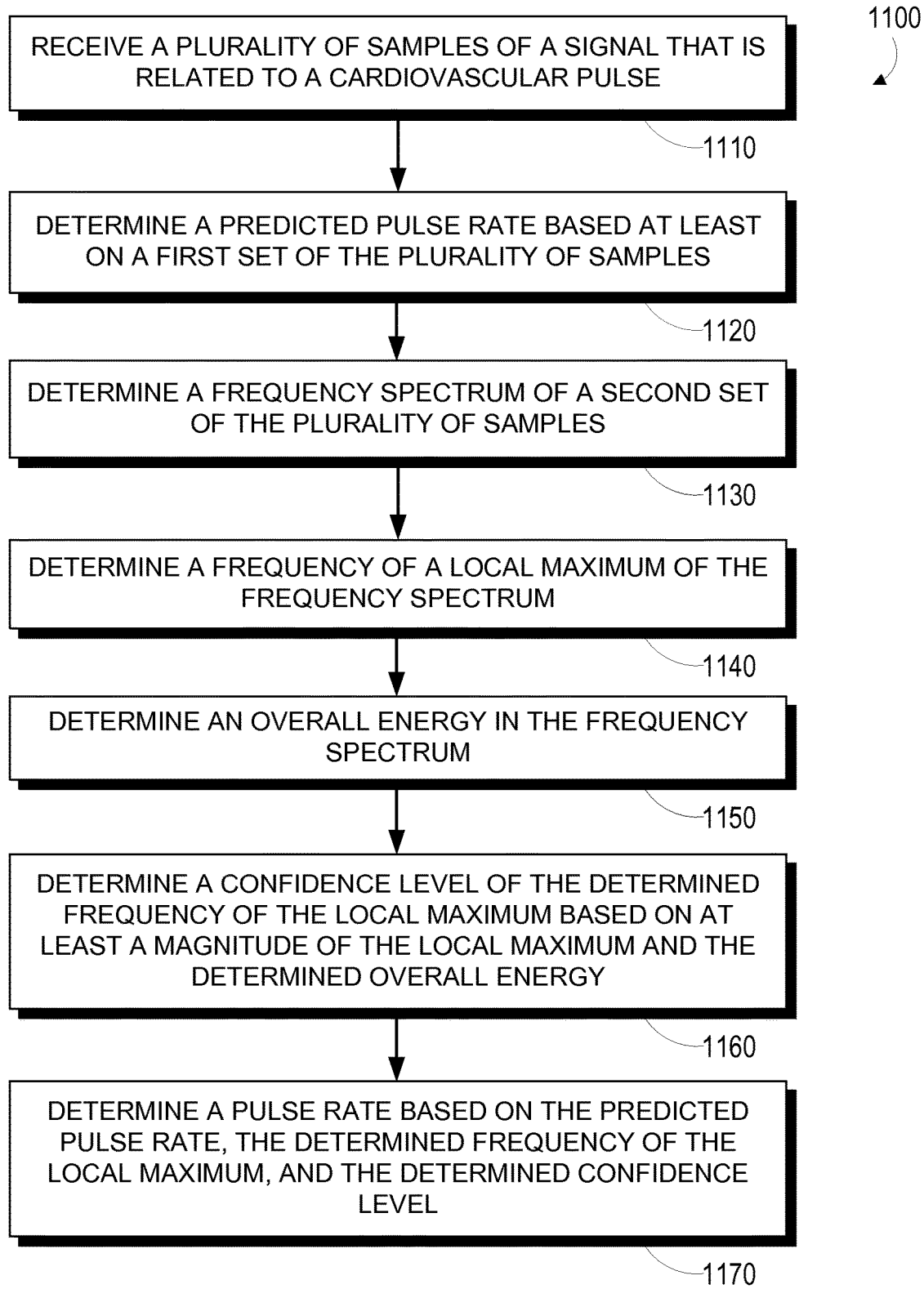
FIG. 11 is a flow chart of an example method.

FIG. 11 is a flowchart of a method 1100 for measuring a cardiovascular pulse rate. The method 1100 includes receiving a plurality of samples of a signal that is related to a cardiovascular pulse (1110). This could include operating a sensor to detect an intensity of light, a pattern of constructive and destructive interference in received light, a pressure, a temperature, an acceleration, a displacement, a color, a flow rate, or some other property related to a cardiovascular pulse, e.g., using a pressure sensor, a light sensor, a light emitter, a tonometer, an ultrasonic transducer, or some other sensing means. In some examples, receiving a plurality of samples of a signal that is related to a cardiovascular pulse (1110) could include receiving a plurality of samples of a plethysmographic signal, i.e., a signal related to a volume of blood in a portion of subsurface vasculature. Receiving such samples could include operating a light source to illuminate the portion of subsurface vasculature and operating a light sensor to detect an intensity of other property of light responsively emitted from the portion of subsurface vasculature.

The method 1100 additionally includes determining a predicted pulse rate based at least on a first set of the plurality of samples (1120). This can include determining a frequency spectrum based on the first set of the plurality of samples and determining a frequency of a maximum of the frequency spectrum. The predicted pulse rate can be determined based on the result of an iterative process, e.g., by performing the steps of the method 1100 for a plurality of different sets of the plurality of samples such that the predicted pulse rate that is based at least on a first set of the plurality of samples is based on further pluralities of samples. The predicted pulse rate could be determined using some other methods.

The method 1100 additionally includes determining a frequency spectrum of a second set of the plurality of samples (1130). Such a determined frequency spectrum can include a plurality of frequency components each having a respective magnitude. This could include performing a discrete frequency transform based on the plurality of samples, e.g., a fast Fourier transform. In some examples, a frequency spectrum of the second set of samples could be determined based on (e.g., by updating) a frequency spectrum determined for an overlapping, prior set of samples, e.g., by performing a sliding discrete frequency transform based on the determined prior frequency spectrum and samples of the second set of the plurality of samples and samples of the overlapping, prior set of samples that are not in common. In some examples, determining a frequency spectrum of a second set of the plurality of samples (1130) could include determining a subset of frequency components of a discrete Fourier transform, e.g., determining a set of frequency components that correspond to frequencies within a specified range of frequencies (e.g., frequencies between approximately 0.5 Hertz and approximately 3.5 Hertz).

The method 1100 additionally includes determining a frequency of a local maximum of the frequency spectrum (1140). This can include determining a maximum magnitude frequency component of the frequency spectrum and determining the frequency corresponding to the determined maximum frequency component. This (1140) can include determining a maximum magnitude frequency component within a range or set of frequency components, e.g., determining a maximum magnitude frequency component of a set of frequency components corresponding to frequencies within a specified range, e.g., a range specified based on an estimated cardiovascular pulse rate determined by operating a plurality of PLLs. This (1140) can include interpolating or otherwise increasing the frequency resolution of the frequency spectrum (e.g., by interpolating the frequency components using a sinc function) and determining a local maximum of the generated interpolated frequency spectrum.

The method 1100 additionally includes determining an overall energy in the frequency spectrum (1150). This could include determining a sum of the magnitudes, a sum of the absolute values of the magnitudes, a sum of the squares of the magnitudes, or performing some other determination based on the frequency components of the frequency spectrum.

The method 1100 additionally includes determining a confidence level of the determined frequency of the local maximum based on at least a magnitude of the local maximum and the determined overall energy (1160). The confidence level could be determined in a variety of ways. For example, the confidence level of the determined frequency could be determined based on a ratio of the squared magnitude of the local maximum and the sum of the squared magnitudes of the frequency components in the frequency spectrum or some other measure of the overall energy in the frequency spectrum.

The method 1100 additionally includes determining a pulse rate based on the predicted pulse rate, the determined frequency of the local maximum, and the determined confidence level (1170). This could include determining a weighted combination of the predicted pulse rate and the determined frequency of the local maximum. Such a weighted combination could be related to an estimate of the rate of change over time of the pulse rate. For example, the weighted average could be determined according to the alpha-beta filter. Such a weighted combination could be based on a weighting factor that is related to the determined confidence level. For example, the pulse rate could be determined using the alpha-beta filter, where the adaptation rate (i.e., the 'alpha' parameter of the alpha-beta filter) is related to such a determined confidence level. Such a weighting factor could be applied to combine the predicted pulse rate and the determined frequency of the local maximum such that higher values of the determined confidence level result in the determined pulse rate being more weighted toward the value of the determined frequency of the local maximum.

The method 1100 could include additional steps or elements in addition to those illustrated in FIG. 11. For example, the method 1100 could include detecting an artifact signal and using the artifact signal to remove unwanted content (e.g., noise content, motion artifact content) of the obtained plurality of samples that is related to the artifact signal. The method 1100 could include indicating a determined pulse rate or other determined information (e.g., frequency spectra, spectrograms) to a user using a user interface. The method 1100 could be performed a plurality of times for a respectively plurality of sets of obtained samples of the signal. Additional and/or alternative steps of the method 1100 are anticipated.

VIII. CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, pulse rates, health states, or other information about the user, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Moreover, it is particularly noted that while devices, systems, methods, and other embodiments are described herein by way of example as being employed to detect cardiovascular pulse rates of a human body, it is noted that the disclosed devices, systems, and methods can be applied in other contexts as well. For example, detection systems configured to determine pulse rates or other frequency information related to oscillating patterns in biosignals or other detected signals may be included in wearable (e.g., body-mountable) and/or implantable devices. In some contexts, such a detection system is situated to be substantially encapsulated by bio-compatible polymeric material suitable for being in contact with bodily fluids and/or for being implanted.

In other examples, devices, systems, and methods disclosed herein may be applied to determine pulse rates or other frequency information related to oscillating patterns in biosignals or other signals detected form or in environments that are not in or on a human body. For example, detection systems disclosed herein may be included devices used to measure cardiovascular pulse rates of an animal.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A method comprising:
receiving, from a sensor, a plurality of samples of a signal, wherein the signal is related to a cardiovascular pulse;
determining a predicted pulse rate based at least on a first set of the plurality of samples;
determining a frequency spectrum of a second set of the plurality of samples, wherein the frequency spectrum comprises a plurality of frequency components, each having a respective magnitude;
determining a frequency of a local maximum of the frequency spectrum;
determining an overall energy in the frequency spectrum;
determining a confidence level of the determined frequency of the local maximum, wherein the determined confidence level is based on at least a magnitude of the local maximum of the frequency spectrum and the determined overall energy in the frequency spectrum; and
determining a pulse rate based on the predicted pulse rate, the determined frequency of the local maximum, and the determined confidence level.

2. The method of claim 1, wherein determining a pulse rate based on the predicted pulse rate, the determined frequency of the local maximum, and the determined confidence level comprises determining a weighted combination of the predicted pulse rate and the determined frequency based on a weighting factor, wherein the weighting factor is based on the determined confidence level such that a higher determined confidence level causes the pulse rate to be more weighted toward the determined frequency of the local maximum.

3. The method of claim 1, wherein determining a predicted pulse rate based at least on a first set of the plurality of samples comprises determining a frequency spectrum of the first set of the plurality of samples, wherein the first set of the plurality of samples and the second set of the plurality of samples overlap, and wherein determining a frequency spectrum of the second set of the plurality of samples comprises performing an update on the determined frequency spectrum of the first set of the plurality of samples based on samples of the second set of the plurality of samples that are not part of the first set of the plurality of samples.

4. The method of claim 3, further comprising:
receiving an artifact signal;
determining a frequency spectrum of the artifact signal; and
filtering the determined frequency spectrum of the second set of the plurality of samples based on the determined frequency spectrum of the artifact signal to generate a plurality of filtered values of the magnitude of the second set of the plurality of samples at the plurality of corresponding different frequencies, wherein determining a frequency of a local maximum of the frequency spectrum comprises determining a frequency of a local maximum of the plurality of filtered values of the magnitude of the second set of the plurality of samples at the plurality of corresponding different frequencies.

5. The method of claim 4, wherein filtering the determined frequency spectrum of the second set of the plurality of samples based on the determined frequency spectrum of the artifact signal comprises applying a least mean squares filter to a portion of the determined frequency spectrum of the second set of the plurality of samples.

6. The method of claim 1, wherein the frequency spectrum of the second set of the plurality of samples includes a specified range of frequencies, wherein the specified range of frequencies is between approximately 0.5 Hertz and approximately 3.5 Hertz.

7. The method of claim 1, wherein determining a frequency of a local maximum of the frequency spectrum comprises:
interpolating the frequency spectrum based on a sinc function; and
determining a frequency of a local maximum of the interpolated frequency spectrum.

8. The method of claim 1, wherein determining the overall energy in the frequency spectrum comprises determining a sum of the squares of the magnitudes of the frequency components in the frequency spectrum, and wherein determining a confidence level of the determined frequency of the local maximum comprises determining a ratio of the determined sum and the magnitude of a particular frequency component that corresponds to the determined local maximum of the frequency spectrum.

9. The method of claim 1, further comprising:
receiving an artifact signal; and
filtering the received plurality of samples of the signal based on the artifact signal to generate a plurality of filtered samples, wherein determining a frequency spectrum of a second set of the plurality of samples comprises determining a frequency spectrum of a set of the plurality of filtered samples that correspond to the second set of the plurality of samples.

10. The method of claim 1 wherein receiving a plurality of samples of a signal comprises:
illuminating a portion of subsurface vasculature; and
receiving light emitted from the portion of subsurface vasculature in response to illumination, wherein the plurality of samples of a signal comprise measurements of the received light at a plurality of respective points in time.

11. A system comprising:
a sensor configured to detect a signal, wherein the signal is related to a cardiovascular pulse; and
a controller operably coupled to the sensor, wherein the controller comprises a computing device programmed to perform controller operations comprising:
operating the sensor to obtain a plurality of samples of the signal;
determining a predicted pulse rate based at least on a first set of the plurality of samples;
determining a frequency spectrum of a second set of the plurality of samples, wherein the frequency spectrum comprises a plurality of frequency components, each having a respective magnitude;
determining a frequency of a local maximum of the frequency spectrum;
determining an overall energy in the frequency spectrum;
determining a confidence level of the determined frequency of the local maximum, wherein the determined confidence level is based on at least a magnitude of the local maximum of the frequency spectrum and the determined overall energy in the frequency spectrum; and
determining a pulse rate based on the predicted pulse rate, the determined frequency of the local maximum, and the determined confidence level.

12. The system of claim 11, wherein the sensor comprises:
a light emitter; and
a light detector, and wherein operating the sensor to obtain a plurality of samples of the signal comprises: (a) operating the light emitter to illuminate a portion of subsurface vasculature and (b) operating the light detector to detect light emitted from the portion of subsurface vasculature in response to illumination at a plurality of points in time, wherein the plurality of samples of the signal comprise measurements of the detected light at respective points in time.

13. The system of claim 11, further comprising an accelerometer, wherein
the controller operations further comprise:
operating the accelerometer to receive an artifact signal;
determining a frequency spectrum of the artifact signal; and
filtering the determined frequency spectrum of the second set of the plurality of samples based on the determined frequency spectrum of the artifact signal to generate a plurality of filtered values of the magnitude of the second set of the plurality of samples at the plurality of corresponding different frequencies, wherein determining a frequency of a local maximum of the frequency spectrum comprises determining a frequency of a local maximum of the plurality of filtered values of the magnitude of the second set of the plurality of samples at the plurality of corresponding different frequencies.

14. The system of claim 11, wherein determining a pulse rate based on the predicted pulse rate, the determined frequency of the local maximum, and the determined confidence level comprises determining a weighted combination of the predicted pulse rate and the determined frequency based on a weighting factor, wherein the weighting factor is based on the determined confidence level such that a higher determined confidence level causes the determined pulse rate to be more weighted toward the determined frequency of the local maximum.

15. The system of claim 11, wherein determining a predicted pulse rate based at least on a first set of the plurality of samples comprises determining a frequency spectrum of the first set of the plurality of samples, wherein the first set of the plurality of samples and the second set of the plurality of samples overlap, and wherein determining a frequency spectrum of the second set of the plurality of samples comprises performing an update on the determined frequency spectrum of the first set of the plurality of samples based on samples of the second set of the plurality of samples that are not part of the first set of the plurality of samples.

16. The system of claim 11, further comprising an accelerometer, wherein the controller operations further comprise:
operating the accelerometer to receive an artifact signal; and
filtering the received plurality of samples of the signal based on the artifact signal to generate a plurality of filtered samples, wherein determining a frequency spectrum of a second set of the plurality of samples comprises determining a frequency spectrum of a set of the plurality of filtered samples that correspond to the second set of the plurality of samples.

17. The system of claim 11, wherein the frequency spectrum of the second set of the plurality of samples includes a specified range of frequencies, wherein the specified range of frequencies is between approximately 0.5 Hertz and approximately 3.5 Hertz.

18. The system of claim 11, wherein determining a frequency of a local maximum of the frequency spectrum comprises:
interpolating the frequency spectrum based on a sinc function; and
determining a frequency of a local maximum of the interpolated frequency spectrum.

19. The system of claim 11, wherein the system includes a user interface, and wherein the controller operations further comprise:
operating the user interface to provide an indication of the determined pulse rate.

20. The system of claim 11, wherein the system comprises a body-mountable device.

* * * * *